US008911798B2

(12) United States Patent
Gupta

(10) Patent No.: US 8,911,798 B2
(45) Date of Patent: Dec. 16, 2014

(54) MULTIVITAMIN AND MINERAL COMPOSITIONS FOR INDIVIDUALS HAVING RENAL DISEASE

(76) Inventor: Ajay Gupta, Henderson, NV (US)

(*) Notice: Subject to any disclaimer, the term of this patent is extended or adjusted under 35 U.S.C. 154(b) by 901 days.

(21) Appl. No.: 12/212,391

(22) Filed: Sep. 17, 2008

(65) Prior Publication Data
US 2009/0074883 A1 Mar. 19, 2009

Related U.S. Application Data

(60) Provisional application No. 60/972,935, filed on Sep. 17, 2007.

(51) Int. Cl.
A01N 59/02 (2006.01)
A23L 1/304 (2006.01)
A23L 1/302 (2006.01)
A23L 1/305 (2006.01)

(52) U.S. Cl.
CPC ............... A23L 1/302 (2013.01); A23L 1/304 (2013.01); A23L 1/3051 (2013.01); A23V 2002/00 (2013.01); Y10S 514/904 (2013.01); Y10S 514/905 (2013.01)
USPC ........................... 424/702; 514/904; 514/905

(58) Field of Classification Search
USPC .................................. 424/702; 514/904, 905
See application file for complete search history.

(56) References Cited

U.S. PATENT DOCUMENTS 2,980,588 A * 4/1961 Larde .............................. 514/52
2004/0137080 A1* 7/2004 Cremisi ......................... 424/702

FOREIGN PATENT DOCUMENTS

WO WO-91/11117 * 8/1991

OTHER PUBLICATIONS

Gleghorn et al., "Observations of vitamin A toxicity in three patients with renal failure receiving parenteral alimentation", Jul. 1986, The American Journal of Clinical Nutrition, vol. 44, pp. 107-112.*
Hathcock et al., "Evaluation of vitmain A toxicity", Aug. 1990, The American Journal of Clinical Nutrition, vol. 52 No. 2, pp. 183-202.*
Angstwurm et al., Selenium replacement in patients with severe systemic inflammatory response syndrome improves clinical outcome. Crit. Care Med., 27: 1807-13 (1999).
Antoniou et al., Reversal of uraemic impotence by zinc. Lancet, 29: 895-8 (1977).
Atkin-Thor et al., Hypoguesia and zinc depletion in chronic dialysis patients. Am. J. Clin. Nutr., 31: 1948 (1978).
Boaz et al., Serum malondialdehyde and prevalent cardiovascular disease in hemodialysis. Kidney Int., 56: 1078-83 (1999).
Bonomini et al., Effects of zinc supplementation in chronic haemodialysis patients. Neph. Dial. Transplant, 8: 1166-8 (1993).
Burk et al., Selenium, an antioxidant nutrient. Nutr. Clin. Care, 5(2): 75-9 (2002).
Cunningham et al., How important is vitamin D deficiency in uremia? Nephroi. Dial. Transplant, 12(1): 16-8 (1997).
DeBari et al., Water soluble vitamins in granulocytes, erythrocytes, and plasma obtained from chronic hemodialysis patients. Am. J. Clin. Nutr., 39(3): 410-5 (1984).
Descombes et al., Water soluble vitamins in chromic hemodialysis patients and need for supplementation. Kindey Int, 43: 1319-28 (1993).
Fournier et al., Importance of vitamin D repletion in uraemia. Nephrol. Dial. Transplant, 14(4): 819-23 (1999).
Giray et al., The effect of vitamin E supplementation on antioxidant enzyme activities and lipid peroxidation levels in hemodialysis patients. Clin. Chim. Acta, 338(1-2): 91-8 (2003).
Gupta et al., Increase risk of hip fractures in U.S. medicare end-stage renal disease patients. J. Am. Soc. Nephrol., 8: 552A (1997).
Ha et al., Abnormal antioxidant vitamin and carotenoid status in chronic renal failure. Quarterly J. Med., 89(10): 765-9 (1996).
Henkin et al., Niacin revisited: Clinical observations on an important but underutilized drug. Am. J. Med., 91(3): 239-46 (1991).
Hodkova et al., Influence of parenteral iron therapy and oral vitamin E supplementation on neutrophil respiratory burst in chronic hemodialysis patients. Ren. Failure, 27(2): 135-41 (2005).
Holben et al., The diverse role of selenium within selenoproteins: a review. J. Am. Diet Assoc., 99(7): 836-43 (1999).
Jamison et al., Design and statistical issues in the homocysteinemia in kidney and end stage renal disease (HOST) study. Clin. Trials, 1(5): 451-60 (2004).
Kimmel et al., Zinc modulates mononuclear cellular calcitriol metabolism in peritoneal dialysis patients. Kidney Int., 49: 1407-12 (1996).
Kohlmeier et al., Bone health of adult hemodialysis patients is related to vitamin K status. Kidney Int., 51(4): 1218-21 (1997).
Livaniou et al., Serum biotin levels in patients undergoing chronic hemodialysis. Nephron, 46(3): 331-2 (1987).
Luo et al., Spontaneous calcification of arteries and cartilage in mice lacking matrix GLA protein. Nature, 386: 78-81 (1997).
Morgan et al., Oxalate metabolism in end-stage renal disease: The effect of ascorbic acid and pyridoxine. Nephrol. Dial. Transplat., 3(1): 28-32 (1988).
Muirhead et al., Zinc metabolism in patients on maintenance hemodialysis. Am. J. Nephrol., 6(6): 422-6 (1986).
Nagasawa et al., Vitamin K2 and serum cholesterol in patients on continuous ambulatory peritoneal dialysis. Lancet, 351(9104): 724 (1998).
Obatake et al., Annual change in bone mineral density in predialysis patients with chronic renal failure: Significance of a decrease in serum 1,25-dihydroxy-vitamin D. J. Bone Miner. Metab., 25(1): 74-9 (2007).

(Continued)

Primary Examiner — Ali Soroush
(74) Attorney, Agent, or Firm — Marshall, Gerstein & Borun LLP

(57) ABSTRACT

The present invention relates to oral compositions which are useful for nutrient supplementation. The dietary supplements and pharmaceutical products and methods of the present invention are particularly useful in the treatment of patients in various stages of chronic kidney disease and supplementing levels of physiological anti-oxidants, vitamins, and minerals in subjects requiring dialysis therapy.

14 Claims, No Drawings

(56) References Cited

OTHER PUBLICATIONS

Rostand, Vitamin B12 levels and nerve conduction velocities in patients undergoing maintenance hemodialysis. *Am. J. Clin. Nutr.*, 29(7): 691-7 (1976).

Sandstead et al., Trace elements in uremia and hemodialysis. *Am. J. Clin. Nutr.*, 33: 1501-8 (1980).

Stein et al., Vitamin levels in chronic renal failure and need for supplementation. *Blood Purif.*, 3(1-3): 52-62 (1985).

Taccone-Gallucci et al., Platelet lipid peroxidation in haemodialysis patients: Effects of vitamin E supplementation. *Nephrol. Dial. Transplant*, 4: 975-8 (1989).

Tarng et al., Intrvenous ascorbic acid as an adjuvant therapy for recombinant erythropoietin in hemodialysis patients with hyperferritinemia. *Kidney Int*, 55: 2477-86 (1999).

Thomson et al., Comparison of trace elements in peritoneal dialysis, hemodialysis, and uremia. *Kidney Int.*, 23(1): 9-14 (1983).

Wallaeys et al., Trace elements in serum, packed cells, and dialysate of CAPD patients. *Kidney Int.*, 30: 599-604 (1986).

Winklhofer-Roob et al., Effects of vitamin E and carotenoid status on oxidative stress in health and disease. Evidence obtained from human intervention studies. *Mol. Aspects Med.*, 24(6): 391-402 (2003).

Yalcin et al., The effect of vitamin E therapy on plasma and erythrocyte lipid peroxidation in chronic hemodialysis patients. *Clin. Chim. Acta*, 185: 109-12 (1989).

Zima et al., Trace elements in end-stage renal disease. 2. Clinical implication of trace elements. *Blood Purif.*, 17(4): 187-98 (1999).

\* cited by examiner

MULTIVITAMIN AND MINERAL COMPOSITIONS FOR INDIVIDUALS HAVING RENAL DISEASE

This application claims the benefit of U.S. Prov. Appl. 60/972,935, filed Sep. 17, 2007, the entire contents of which are incorporated herein by reference.

FIELD OF THE INVENTION

The present invention relates to oral compositions which are useful for nutrient supplementation. The dietary supplements and pharmaceutical products and methods of the present invention are particularly useful in the treatment of uremia and supplementing levels of physiological anti-oxidants, vitamins, and minerals in subjects requiring such therapy.

BACKGROUND OF THE INVENTION

The kidneys perform a variety of excretory, metabolic, regulatory, and endocrine functions. They control fluid and electrolyte homeostasis, excretion of metabolic waste products, and synthesis and degradation of several hormones. The kidneys also maintain a homeostatic plasma composition.

Renal failure can occur in a patient due to a variety of diseases and insults. Acute renal failure can result from direct renal tubular injury, renal ischemia, and intra-tubular obstruction. Chronic renal disease is progressive, necessitating repeated monitoring over time and appropriate modification of therapeutic interventions to compensate for progressive loss of kidney function. Renal failure results in diminished glomerular filtration and reduced secretion of metabolic waste products, water and electrolytes. To minimize the accumulation of these solutes, either dietary modification (to reduce their supply/production) or dialysis (to remove them from the blood) is necessary. When renal function has decreased to less than about 10% to 5% of normal, the kidneys lose their ability to perform their excretory functions. In the absence of renal replacement therapy (dialysis or transplantation), resultant fluid overload, electrolyte imbalances, and uremic syndrome can result in death.

In the United States, there are about 2.5 million patients with varying degrees of renal failure (serum creatinine>1.7 mg/dL). Approximately 300,000 of these patients require dialysis. Globally, there are approximately 300,000 dialysis patients in Europe, 20,000 in Canada, 11,000 in Australia and New Zealand, 170,000 in Japan, 80,000 in Latin America, 45,000 in Asian Pacific region, and 50,000 in China and India. The dialysis population is growing on an average at a rate of 8% per year. Of the patients in the U.S. and Europe, the majority of patients on dialysis and a variable proportion of pre-dialysis patients are prescribed multivitamin supplements.

Dietary restrictions are a cornerstone in the medical management of renal patients. Nutritional interventions in end-stage renal disease have two primary goals: (1) minimize or prevent the characteristic uremic symptoms, and (2) achieve and maintain optimal nutritional status. Control of dietary protein and maintaining non-protein caloric intake are the highest priorities. Typically, modifications in dietary phosphorus, fluid, potassium, and/or sodium intakes are also necessary to limit their accumulation in the blood or the development of hypertension.

Nutritional management in renal disease presents a number of challenges for clinicians, since renal disease can both directly and indirectly influence nutritional status. The direct effects result from alteration in the metabolism of specific nutrients. Compared with the nutritional requirements of normal healthy individuals, renal patients undergoing dialysis require more protein, calcium, folic acid and pyridoxine, while the consumption of vitamins A, C and phosphorus, magnesium, sodium, potassium, and fluids typically must be controlled.

Indirect effects of renal disease reflect, at least in part, alterations in the redox status of the body, since renal disease exemplifies one of several disease states in which the individual experiences chronic oxidative stress. The normal anti-oxidant defense system depends on the synergic interactions of multiple anti-oxidants for optimal protection against damaging radicals. Patients with chronic kidney disease have multiple abnormalities in their anti-oxidant profiles, including reported deficiencies in enzymic anti-oxidants, selenium, ascorbate, circulating vitamin E and carotenoids.

Further, loss of renal function affects nearly all other organ systems, including the heart, nerves, brain, blood vessels, gonadal function. Uremic symptoms of nausea, loss of taste, vomiting, anorexia, malaise, and pruritus may interfere directly with food preparation and consumption by renal patients and may aggravate losses of vitamins or trace minerals. These changes lead to malnutrition including a decrease in the uptake of vitamins and minerals (e.g., riboflavin, folate, and vitamin D).

In this patient population, dietary restrictions to limit the intake of potassium and phosphorus necessitate restricted intake of green vegetables, fruits and fruit juice. Dietary restrictions on fruits and vegetables may lead to deficiencies in vitamins that are obtained solely or primarily from dietary sources, e.g., ascorbate, alpha-tocopherol, and carotenoids (including lycopene, alpha-carotene, beta-carotene, and lutein). Dietary restrictions requested of a renal patient make dietary compliance difficult. The dietary restrictions complicate food selection, and patients often must substantially change their eating patterns. As a consequence, the patient's diet may become nutritionally inadequate, requiring selective vitamin and mineral supplementation to prevent deficiencies. A low-protein diet, for example, limits intake of zinc, iron, calcium, vitamin C, folate, and other B vitamins. Therefore, end-stage renal disease (ESRD) patients receiving maintenance dialysis are at elevated risk for developing vitamin and mineral deficiency.

Elevated vitamin A levels in renal patients have been reported even in the absence of supplements, and symptoms of clinical toxicity have been reported. Hypervitaminosis A is associated with increased serum calcium, triglycerides, and cholesterol and may heighten susceptibility to fractures. To minimize toxic levels, dietary vitamin A intake in renal patients should be at or below the RDI. Therefore, vitamin supplements prescribed for patients with chronic kidney disease need to be devoid of vitamin A.

In the United States, the major dietary source of the vitamin is milk that is fortified with either ergocholecalciferol or cholecalciferol. Natural sources of vitamin D are fatty fish, fish liver oil, and to a lesser extent, eggs. Because of dietary restrictions on dairy products, many chronic kidney disease (CKD) patients have a low dietary supply of vitamin D and are therefore dependent on endogenous synthesis of vitamin D in skin to maintain their requirement for this essential vitamin. Solar UV-B radiation (290-315 nm) initiates cutaneous synthesis of vitamin D by the photoconversion of 7-dehydrocholesterol to precholecalciferol. Then, over a period of 1-2 days at body temperature, precholecalciferol spontaneously isomerizes to cholecalciferol. UV-B radiation is a component of sunlight but is not usually a significant part of indoor lighting. Limited exposure to sunlight and dietary restrictions on dairy products may predispose CKD patients to vitamin D deficiency. Loss of cholesterol from the skin in the elderly impairs skin synthesis of this important vitamin. The proportion of ESRD patients that are more than 65 years of age continues to increase. Consequently, ESRD patients are likely to have an increased incidence of vitamin D deficiency compared to other individuals. The conversions by the kidney of vitamin D to the most biologically active form, $1,25(OH)_2D_3$, is reduced in renal patients. As a consequence of the calcium, phosphate and vitamin D imbalance, bone disease and hyperparathyroidism are common findings in patients with advanced renal disease.

Vitamin E is present in leafy green and deep yellow vegetables, meat, the yolk of the egg, fruit, milk, and dairy products. While meat is restricted in uremic patients because of its atherogenic potential, the other food items listed above are restricted in dialysis patients because of their phosphorus and/or potassium content. Consequently, dialysis patients are often deficient in vitamin E.

In addition, ESRD patients typically undergo dialysis multiple times each week, and water soluble vitamins are lost during each dialysis procedure. In the past ten years the dialysis practice has changed considerably. As compared to a decade ago, today patients are dialyzed longer, using better vascular accesses and higher blood flows. Further, dialyzers with higher efficiency/flux and larger surface areas are used. Consequently, there has been an increase in the quantities of vitamins that are removed during dialysis.

Further, the average age of incident dialysis patients in the United States is 60 years, and 32% of all dialysis patients are over 65 years of age. The elderly often have poor nutritional intake and impaired nutrient absorption from the gastrointestinal tract and therefore require higher daily intake of vitamins to maintain adequate vitamin status. With increasing age of an incident dialysis patient, cardiovascular disease has reached epidemic proportions in this patient population. Furthermore, sicker patients are being dialyzed.

Aluminum accumulation in the brain and bones in renal patients has been suggested as a potential cause of the osteodystrophy and encephalopathy occurring in renal patients. A typical diet provides 2 to 100 mg of aluminum per day. Normally, the intestine is relatively impermeable to aluminum, and most dietary aluminum is excreted in the stool. Persons with renal insufficiency, particularly those receiving aluminum-containing medications, have substantially elevated blood aluminum concentrations because while absorption is unchanged, urinary excretion is greatly reduced. Citrate readily solubilizes aluminum, facilitating both its absorption and distribution throughout the body.

For all of these reasons and others not presented herein, malnutrition is very common co-morbid condition in the dialysis patient population. Oral multivitamin and mineral supplements present an optimal way to address dietary deficiencies such as those described above, and it has been a common practice in the United States and Europe to prescribe multivitamins for all patients with kidney failure, especially for those patients receiving maintenance dialysis.

TABLE 1

Vitamins and minerals and concise descriptions of their physiological activities
(Source:wikipedia)

| Composition | Concise Description of Physiological Activity |
| --- | --- |
| Vitamin A | An essential human nutrient that is found as any of these forms: (a) retinol, the animal form of vitamin A, is a yellow fat-soluble, antioxidant vitamin with importance in vision and bone growth, it belongs to the family of chemical compounds known as retinoids; (b) other retinoids, a class of chemical compounds that are related chemically to vitamin A; and (c) carotenoids or other substances that enable the body to synthesize retinoids. |
| Vitamin C | A water-soluble, essential nutrient required in small amounts in order to allow a range of essential metabolic reactions in animals and plants. Chemically, ascorbic acid exists in two forms: the active reduced form is ascorbic acid, while the oxidized form is dehydroascorbic acid. Dehydroscorbic acid present in the diet can be reduced to the active form in the body by enzymes and glutathione. Ascorbic acid is an antioxidant and protects the body against oxidative stress, as well as being needed as a coenzyme in some enzymatic reactions. |
| Vitamin D | A group of fat-soluble prohormones, the two major forms of which are vitamin $D_2$ (or ergocalciferol) and vitamin $D_3$ (or cholecalciferol). The term vitamin D also refers to metabolites and other analogues of these substances. Vitamin $D_3$ is produced in skin exposed to sunlight, specifically ultraviolet B radiation. Vitamin D plays an important role in the maintenance of several organ systems. Vitamin D regulates the calcium and phosphorus levels in the blood by promoting their absorption from food in the intestines, and by promoting re-absorption of calcium in the kidneys. It promotes bone formation and mineralization and is essential in the development of an intact and strong skeleton. It inhibits parathyroid hormone secretion from the parathyroid gland. Vitamin D affects the immune system by promoting immunosuppression and anti-tumor activity. |
| Vitamin E | A fat-soluble vitamin and anti-oxidant that is provided in eight stereoisomeric forms. All of the forms have a chromanol ring, with a hydroxyl group which can donate a hydrogen atom to reduce free radicals and a hydrophobic side chain which allows for penetration into biological membranes. There is an alpha, beta, gamma and delta form of both the tocopherols and tocotrienols, determined by the number of methyl groups on the chromanol ring. Each form has its own biological activity, the measure of potency or functional use in the body. |

TABLE 1-continued

Vitamins and minerals and concise descriptions of their physiological activities
(Source:wikipedia)

| Composition | Concise Description of Physiological Activity |
| --- | --- |
| Vitamin K | A group of lipophilic, and hydrophobic, vitamins that are needed for the posttranslational modification of certain proteins, mostly required for blood coagulation. Chemically they are 2-methyl-1,4-naphthoquinone derivatives. Vitamin $K_2$ (menaquinone, menatetrenone) is normally produced by bacteria in the intestines, and dietary deficiency is extremely rare unless the intestines are heavily damaged. High concentrations of these quinines crosslink proteins and adversely affect red cell viability. |
| Thiamin/Vitamin $B_1$ | As the pyrophosphate (TPP), a coenzyme for pyruvate dehydrogenase, α-ketoglutarate dehydrogenase, branched-chain alpha-keto acid dehydrogenase, and transketolase. The first two of these enzymes function in the metabolism of carbohydrates, while transketolase functions in the pentose phosphate pathway to synthesize NADPH and the pentose sugars deoxyribose and ribose. In general, TPP functions as a cofactor for enzymes that catalyze the dehydrogenation (decarboxylation and subsequent conjugation to Coenzyme A) of alpha-keto acids. TPP is synthesized by the enzyme thiamine pyrophosphokinase, which requires free thiamine, magnesium, and adenosine triphosphate. |
| Riboflavin/Vitamin $B_2$ | An easily absorbed micronutrient with a key role in maintaining health in animals. It is the central component of the cofactors FAD and FMN, and is therefore required by all flavoproteins. As such, vitamin $B_2$ is required for a wide variety of cellular processes. Like the other B vitamins, it plays a key role in energy metabolism, and is required for the metabolism of fats, carbohydrates, and proteins. |
| Niacin/Vitamin $B_3$ | A water-soluble vitamin whose derivatives such as NADH, NAD, $NAD^+$, and NADP play essential roles in energy metabolism in the living cell and DNA repair. The designation vitamin $B_3$ also includes the corresponding amide nicotinamide, or niacinamide. |
| Pantothenic Acid/Vitamin $B_5$ | A water-soluble vitamin required to sustain life. Pantothenic acid is needed to form coenzyme-A (CoA), and is critical in the metabolism and synthesis of carbohydrates, proteins, and fats. |
| Vitamin $B_6$ | A water-soluble vitamin that is present in the body as seven forms: pyridoxine (PN), pyridoxine 5'-phosphate (PNP), pyridoxal (PL), pyridoxal 5'-phosphate (PLP), pyridoxamine (PM), pyridoxamine 5'-phosphate (PMP), and 4-pyridoxic acid (PA). PN is the form that is given as vitamin B6 supplement, PLP is the metabolically active form and PA is the catabolite which is excreted in the urine. All forms except PA can be interconverted. PLP is a cofactor in many reactions of amino acid metabolism. PLP also is necessary for the enzymatic reaction governing the release of glucose from glycogen. |
| Biotin/Vitamin $B_7$ | A water-soluble B-complex vitamin which is important in the catalysis of essential metabolic reactions to synthesize fatty acids, in gluconeogenesis, and to metabolize leucine. |
| Folate/Vitamin $B_9$ | A water-soluble vitamin which in its oxidized and reduced forms are substrates in a number of single-carbon-transfer reactions, and also are involved in the synthesis of dTMP (2'-deoxythymidine-5'-phosphate) from dUMP (2'-deoxyuridine-5'-phosphate). It helps convert vitamin B12 to one of its coenzyme forms and helps synthesize the DNA required for all rapidly growing cells. |
| Vitamin $B_{12}$ Source | A fat-soluble, cobalt-containing vitamin typically provided as cyanocobalamin, a compound that is metabolized to a vitamin in the B complex commonly known as vitamin $B_{12}$ (or $B_{12}$ for short). The name vitamin $B_{12}$ is used in two different ways. In a broad sense it refers to a group of cobalt-containing compounds known as cobalamins-cyanocobalamin (an artifact formed as a result of the use of cyanide in the purification procedures), hydroxocobalamin and the two coenzyme forms of $B_{12}$, methylcobalamin ($MeB_{12}$) and 5-deoxyadenosylcobalamin (adenosylcobalamin-$AdoB_{12}$). |
| Choline | A nutrient, essential for cardiovascular and brain function, and for cellular membrane composition and repair. |
| Calcium | An element essential in muscle contraction, oocyte activation, bones and tooth structure, blood clotting, nerve impulse transmission, regulating heartbeat, and fluid balance within cells. |
| Iron | A necessary trace element used by all known living organisms. Iron-containing enzymes, usually containing heme prosthetic groups, participate in catalysis of oxidation reactions in biology, and in transport of a number of soluble gases. |
| Phosphorus | A component of DNA and RNA and essential element for all living cells. |

TABLE 1-continued

Vitamins and minerals and concise descriptions of their physiological activities (Source:wikipedia)

| Composition | Concise Description of Physiological Activity |
|---|---|
| Iodine | An essential trace element; its only known roles in biology are as constituents of the thyroid hormones, thyroxine (T4) and triiodothyronine (T3). Thyroid hormones play a very basic role in biology, acting on gene transcription to regulate the basal metabolic rate. The total deficiency of thyroid hormones can reduce basal metabolic rate up to 50%, while in excessive production of thyroid hormones the basal metabolic rate can be increased by 100%. T4 acts largely as a precursor to T3, which is (with some minor exceptions) the biologically active hormone. |
| Magnesium | A mineral essential to the basic nucleic acid chemistry of life, and thus is essential to all cells of all known living organisms. |
| Zinc | A mineral that is present in enzymes active in gene expression. It may also possess anti-oxidant properties, which protect against premature aging of the skin and muscles of the body. |
| Selenium | A substituent which is present in the active center of certain anti-oxidant enzymes, which likely are necessary for the function of all cells. |
| Copper | An essential nutrient found primarily in the bloodstream, as a cofactor in various enzymes, and in copper-based pigments. Effectively absorbed through the skin. |
| Manganese | An essential trace nutrient in all forms of life. The classes of enzymes that have manganese cofactors are very broad and include such classes as oxidoreductases, transferases, hydrolases, lyases, isomerases, ligases, lectins, and integrins. The best known manganese-containing polypeptides may be arginase, the diphtheria toxin, and Mn-containing superoxide dismutase (Mn-SOD) |
| Chromium | A trace element which in its trivalent form (Cr(III), or $Cr^{3+}$) is required in trace amounts for sugar metabolism in humans. |
| Molybdenum | A cofactor of the enzyme xanthine oxidase which is involved in the pathways of purine degradation and formation of uric acid. In some animals, adding a small amount of dietary molybdenum enhances growth. |

After considering price and availability, renal patients may initially select and use an over-the-counter multivitamin preparation, in other words, a dietary supplement nutritional product designed to meet the nutrient requirements of normal healthy individuals, rather than one that is appropriate for the individual's disease state. Over-the-counter multivitamin products such as the products described in Table 2 provide quantities of vitamins A, D, and C, magnesium, phosphorus, and possibly sodium and potassium that may greatly exceed the needs of a renal patient. Frequently, these conventional supplements do not meet the increased calcium, pyridoxine, and folic acid requirements of a renal patient. In addition, these products contain additional minerals that present toxicity risks for renal patients, such as chromium, iron, and tin. Conventional over-the-counter supplement formulations may contain lake dyes that are sources of metals such as aluminum that are toxic when provided to renal patients.

TABLE 2

Recommended Daily Intake of vitamins and minerals in the general population and comparison to typical "over-the-counter" multivitamin & mineral products

| | | Concentration per Unit Dose | |
|---|---|---|---|
| Composition | Recommended Daily Intake (RDI) | Myadec ® tablet* | Centrum ® Silver ® tablet* |
| Vitamin A | 5,000 IU | 5,000 IU (as Vitamin A acetate and beta-carotene) | 3,500 IU (29% as beta-carotene) |
| Vitamin C | 60 mg | 60 mg | 60 mg |
| Vitamin D | 400 IU | 400 IU (as ergocalciferol) | 400 IU |
| Vitamin E | 30 IU | 30 IU | 45 IU |
| Vitamin K | 80 mcg | 25 mcg (as phytonadione) | 10 mcg |
| Thiamin/Vitamin $B_1$ | 1.5 mg | 1.7 mg (as thiamin mononitrate) | 1.5 mg |
| Riboflavin/Vitamin $B_2$ | 1.7 mg | 2 mg | 1.7 mg |
| Niacin/Vitamin $B_3$ | 20 mg | 20 mg | 20 mg |
| Pantothenic Acid/Vitamin $B_5$ | 10 mg | 10 mg | 10 mg |
| Vitamin $B_6$ | 2 mg | 3 mg | 3 mg |
| Biotin/Vitamin $B_7$ | 300 mcg | 30 mcg | 30 mcg |
| Folate/Vitamin $B_9$ | 400 mcg | 400 mcg | 400 mcg |
| Vitamin $B_{12}$ Source | 6 mcg | 6 mcg | 25 mcg |

TABLE 2-continued

Recommended Daily Intake of vitamins and minerals in the general population and comparison to typical "over-the-counter" multivitamin & mineral products

| Composition | Recommended Daily Intake (RDI) | Myadec ® tablet* | Centrum ® Silver ® tablet* |
|---|---|---|---|
| Choline | (No recommendation) | | |
| Calcium | 1,000 mg | 162 mg (as calcium phosphate) | 200 mg |
| Iron | 18 mg | 18 mg (as ferrous fumarate) | |
| Phosphorus | 1,000 mg | 125 mg | 48 mg |
| Iodine | 148 mcg | 150 mcg (as KI) | 150 mcg |
| Magnesium | 400 mg | 100 mg (as MgO) | 100 mg |
| Zinc | 15 mg | 15 mg (as zinc oxide) | 15 mg |
| Selenium | 68 mcg | 25 mcg (as sodium selenate) | 20 mcg |
| Copper | 2 mg | 2 mg (as CuO) | 2 mg |
| Manganese | 2 mg | 2.5 mg | 2 mg |
| Chromium | 120 mcg | 25 mcg | 150 mcg |
| Molybdenum | 75 mcg | 25 mcg (as sodium molybdate) | 75 mcg |
| Other Components | Recommended Daily Intake Not Established | Chloride - 36 mg<br>Potassium - 40 mg<br>Nickel - 5 mcg (as $NiSO_4$)<br>Tin - 10 mcg (as $SnCl_2$)<br>Silicon - 10 mcg<br>Vanadium - 10 mcg (as sodium metavanadate)<br>Boron - 150 mcg<br>Cellulose<br>Gelatin<br>Copovidone<br>Croscarmellose Sodium<br>Dextrin<br>Stearic Acid<br>Magnesium stearate<br>Polyethylene glycol<br>Corn starch<br>FD&C Red No. 40 Lake<br>FD&C Blue No. 1 Lake<br>FD&C Yellow No. 6 Lake<br>Glucose<br>Hypromellose<br>Acacia<br>Resin<br>Titanium oxide<br>Soy | Potassium - 80 mg<br>Chloride 72 mg<br>Boron 150 mcg<br>Nickel 5 mcg<br>Silicon 2 mg<br>Vanadium 10 mcg<br>Lutein 250 mcg<br>Lycopene 300 mcg |

*Centrum ® Silver ® is a brand name for an adult multivitamin supplement manufactured by Wyeth Consumer Healthcare. Myadec ® is a brand name for an adult multivitamin supplement manufactured by McNeil-PPC. IU is International Units; mg is milligrams; mcg is micrograms.

Nephrologists often prescribe to pre-dialysis patients the same multivitamin preparation that they prescribe to dialysis patients. The conventional vitamin preparations that are currently used in this patient population (Table 3) are similar in composition to preparations that were in use about 15 years ago.

TABLE 3

Typical conventional multivitamin and mineral preparations that are prescribed to Stage IV and V renal disease patients

| Composition | Nephrocaps ® soft-gel capsule | RENAX ® 5.5 tablet (Note 2) | DIATX ® tablet | DIATX ® Zn tablet | Dialyvite ® 3000 tablet | Dialyvite with zinc tablet |
|---|---|---|---|---|---|---|
| Ascorbic Acid/ Vitamin C | 100 mg | 100 mg | 60 mg | 60 mg | 100 mg | 100 mg |
| Vitamin E | | 35 IU | | | 30 IU | |
| Thiamine/ Vitamin $B_1$ | 1.5 mg | 3 mg | 1.5 mg | 1.5 mg | 1.5 mg | 1.5 mg |
| Riboflavin/ Vitamin $B_2$ | 1.7 mg | 2 mg | 1.5 mg | 1.5 mg | 1.7 mg | 1.7 mg |

TABLE 3-continued

Typical conventional multivitamin and mineral preparations that are prescribed to Stage IV and V renal disease patients

| | Concentration per Unit Dose | | | | | |
|---|---|---|---|---|---|---|
| Composition | Nephrocaps ® soft-gel capsule | RENAX ® 5.5 tablet (Note 2) | DIATX ® tablet | DIATX ® Zn tablet | Dialyvite ® 3000 tablet | Dialyvite with zinc tablet |
| Niacin/Vitamin $B_3$ | 20 mg | 20 mg (Note 1) | 20 mg (Note 1) | 20 mg (Note 1) | 20 mg | 20 mg |
| Pantothenic Acid/Vitamin $B_5$ | 5 mg | 10 mg | 10 mg | 10 mg | 10 mg | 10 mg |
| Pyridoxine HCl/ Vitamin $B_6$ | 10 mg | 30 mg | 50 mg | 50 mg | 25 mg | 10 mg |
| Biotin/Vitamin $B_7$ | 150 mcg | 300 mcg | 300 mcg | 300 mcg | 300 mcg | 300 mcg |
| Folate/Vitamin $B_9$ | 1 mg | 5.5 mg | 5 mg | 5 mg | 3 mg | 1 mg |
| Vitamin $B_{12}$ Source | 6 mcg | 1 mg | 1 mg | 2 mg | 1 mg | 6 mcg |
| Zinc | | 20 mg | | 25 mg Zn (as ZnO) | 15 mg | 50 mg |
| Selenium | | 70 mcg | | | 70 mcg | |
| Other Components | | | | 1.5 mg Cu (as copper gluconate) | | |

Nephrocaps ® Dialysis/Stress Vitamin (a brand of vitamin marketed as a medical food by Fleming & Company Pharmaceuticals, Fenton, MO)
RENAX ® 5.5 (a brand of multivitamin marketed as a medical food by Everett Laboratories, West Orange, NJ)
DIATX ® and DIATX ® with zinc (brands of vitamins marketed as medical foods by PamLab LLC, Covington, LA)
Dialyvite ® 3000 and Dialyvite ® with Zinc (prescription products marketed as a medical food by Hillestad Pharmaceuticals, Dialyvite Division, Woodruff, WI)

However, research over the last decade has made it apparent that dialysis patients require vitamin and mineral supplementation that is different from that of pre-dialysis patients and individuals who do not have renal disease. For example, elevated vitamin A levels in renal patients have been reported even in the absence of supplements, and symptoms of clinical toxicity have been reported. Hypervitaminosis A is associated with increased serum calcium, triglycerides, and cholesterol and may heighten susceptibility to fractures. Conventional vitamin and mineral supplements either include large doses of Vitamin A (Table 2) or do not provide carotenoid substitutes for Vitamin A. Hyperhomocysteinemia is universally present in dialysis patients. Hyperhomocysteinemia has been associated with increased risk of vascular disease including coronary, peripheral and cerebrovascular disease. Folic acid (Vitamin B9) in a dose of 1 mg/day may not be sufficient, but higher daily doses of folic acid can lower plasma homocysteine levels in up to 30% of renal patients. Conventional vitamin and mineral supplements may provide folate at the indicated doses but only as part of a formulation that is inappropriate for renal patients (Tables 2 and 3). Higher efficiency of dialysis leads to increased removal of ascorbic acid (vitamin C). Conventional vitamin and mineral supplements frequently provide inadequate doses of vitamin C (Tables 2 and 3). Likewise, Vitamin D deficiency is common in dialysis patients, and its correction is important to prevent renal bone disease. Conventional vitamin and mineral supplements either lack Vitamin D (Table 3) or provide it as part of a formulation that is inappropriate for renal patients (Table 2). Vitamin E deficiency is not uncommon in dialysis patients, and vitamin E supplementation is advisable to prevent atherosclerotic vascular disease. Conventional vitamin and mineral supplements either lack Vitamin E (Table 3) or provide it as part of a formulation that is inappropriate for renal patients (Table 2). Vitamin K is important for bone health. Dialysis patients are at risk for vitamin K deficiency due to undernutrition and frequent antibiotic exposure. Therefore, small doses of vitamin K are indicated in dialysis patients as part of their multivitamin formulation. Conventional vitamin and mineral supplements either lack Vitamin K (Table 3) or provide it as part of a formulation that is inappropriate for renal patients (Table 2). Zinc deficiency is common in dialysis patients and may lead to impairment of immune response, loss of hair, loss of libido, impotence, loss of taste, muscle weakness etc. Conventional vitamin and mineral supplements either lack zinc (Table 3) or provide it as part of a formulation that is inappropriate for renal patients (Table 2).

GENERAL DESCRIPTION OF THE INVENTION

For patients with renal failure, who are at risk of deficiency and subsequent complications because of their dietary limitations and altered metabolism, vitamin and micronutrient supplementation that is appropriate to the disease state is a significant unmet need. The shortcomings exhibited by conventional multivitamin and mineral compositions in meeting the nutritional needs of individuals with kidney disease have been described above. The novel compositions and related methods of the present invention comprise a unique mixture of vitamins and minerals that are useful as nutritional supplements for treating individuals suffering from renal disease.

The present invention provides nutritional compositions and methods of using said compositions for treating individuals with renal disease. Specifically, the present invention discloses novel compositions of vitamins and minerals in amounts that can be used to supplement the nutrients that are deficient in patients afflicted with renal disease, renal insufficiency, or end-stage renal disease. The compositions of the present invention can also be used as nutritional supplements for patients undergoing dialysis therapy or for patients on a restricted diet. In addition, the compositions can be used to treat the nutritional deficiencies of any disease state that results in increased oxidative stress, elevated cholesterol levels, or elevated homocysteine levels.

The compositions of the present invention comprise numerous vitamins and minerals that will improve the nutritional state of an individual having compromised renal function. The vitamins of the present invention comprise carotenoids, vitamin C, vitamin D, vitamin E, vitamin K, vitamin B1, vitamin B2, vitamin B3, vitamin B5, vitamin B6, vitamin B7, vitamin B9, and vitamin B12. The minerals of the present invention comprise selenium and zinc. Antioxidant amino acids of the present invention comprise L-cysteine and glutathione.

The present invention also relates to methods for supplementing the nutritional deficiencies in a patient comprising the step of administering to said patient a composition comprising carotenoids, vitamin C, vitamin D, vitamin E, vitamin K, vitamin B1, vitamin B2, vitamin B3, vitamin B5, vitamin B6, vitamin B7, vitamin B9, vitamin B12, selenium, and zinc. Optionally, the composition further comprises the anti-oxidant amino acids L-cysteine and glutathione. The compositions used in the methods of the present invention may further comprise a pharmaceutically acceptable carrier. In a preferred embodiment, the compositions of the present invention are administered to said patient orally and preferably on a daily basis. In hemodialysis patients the multivitamins may be prescribed to be taken only after dialysis in order to compensate for the dialytic loss of water soluble vitamins. On the other hand, in peritoneal dialysis patients undergoing cycling peritoneal dialysis at night the multivitamin may be best prescribed in the morning.

DETAILED DESCRIPTION

The nutritional therapy of individuals with renal disease requires unique compositions of vitamins and minerals due to the multiple metabolic and biochemical changes that accompany the disease, as well as dietary restrictions that are a part of treatment. The primary object of the invention is to provide multivitamin and mineral compositions that meet the unique nutritional needs of patients with kidney disease. As compared to conventional multivitamin and mineral formulations, the compositions of the invention are characterized by: 1) the replacement of Vitamin A by carotenoids; 2) the addition of fat soluble vitamins including D, E, and K; 3) higher doses of vitamin C and folic acid; 4) the addition of trace metals (including zinc and selenium); 5) the addition of anti-oxidant amino acids or their metabolic precursors (including L-cysteine and glutathione); and 6) unique combinations of vitamins and anti-oxidants that act synergistically to mitigate the adverse effects of oxidative stress and uremia.

The compositions of the present invention comprise numerous vitamins and minerals that will improve the nutritional state of an individual having compromised renal function. The vitamins of the present invention comprise carotenoids, vitamin C, vitamin D, vitamin E, vitamin K, vitamin $B_1$, vitamin $B_2$, vitamin $B_3$, vitamin $B_5$, vitamin $B_6$, vitamin $B_7$, vitamin $B_9$, and vitamin $B_{12}$. The minerals of the present invention comprise selenium and zinc. Antioxidant amino acids of the present invention comprise L-cysteine and glutathione.

The term "renal disease" is a generic expression encompassing an array of disorders that afflict the kidneys. The term "renal patient" includes patients suffering from renal disease. KDOQI (Kidney Disease Outcomes Quality Initiatives), an effort to improve patient outcomes through the development of clinical practice guidelines, defines chronic kidney disease (CKD) according to the presence or absence of markers of kidney damage and the level of kidney function (glomerular filtration rate [GFR])—irrespective of the type of kidney disease (the specific diagnosis). [www.kidney.org/professionals/KLS/aboutCKD.cfm.] Five stages of CKD are recognized in the KDOQI (Table 4).

TABLE 4

Five stages of renal disease

| Stage | Glomerular Filtration Rate (GFR), mL/min/1.73 m$^2$ |
| --- | --- |
| 1 | 90+ (Kidney damage with near normal GFR) |
| 2 | 60-89 (Mildly reduced renal function) |
| 3 | 30-59 (Moderately reduced renal function) |
| 4 | 15-29 (Severely reduced renal function) |
| 5 | <15 (End Stage Renal Disease) |

The term "carotenoids" means the tetraterpenoid family of natural substances and includes both xanthophylls and carotenes. Xanthophylls are exemplified by lutein and zeaxanthin. The carotenes include alpha-carotene, beta-carotene and lycopene.

The terms "treating" and "treatment" and the like are used herein to generally mean obtaining a desired pharmacological and physiological effect. The effect may be prophylactic in terms of preventing or partially preventing a disease, symptom or condition thereof and/or may be therapeutic in terms of a partial or complete cure of a disease, condition, symptom or adverse effect attributed to the disease. The term "treatment" as used herein encompasses any treatment of a disease in a mammal, particularly a human and includes: (a) preventing the disease from occurring in a subject which may be predisposed to the disease but has not yet been diagnosed as having it; (b) inhibiting the disease or arresting its development; (c) relieving the disease, causing regression of the disease and/or its symptoms or conditions; or (d) returning a clinical value to the concentration range normally found in a subject.

The phrase "therapeutically effective" is intended to qualify the amount of a nutrient which will achieve the goal of abating, mitigating, reducing or preventing a deficiency disorder, or of restoring physiologically adequate concentrations of nutrients while avoiding adverse side effects typically associated with repletion.

The terms "mg" and "mcg" are abbreviations for milligrams and micrograms, respectively. The term "IU" is the abbreviation for International Units.

Compositions of the present invention comprise numerous vitamins and minerals that will improve the nutritional state of an individual having compromised renal function. Therefore, compositions of the invention comprise carotenoids, vitamin C, vitamin D, vitamin E, vitamin K, vitamin $B_1$, vitamin $B_2$, vitamin $B_3$, vitamin $B_5$, vitamin $B_6$, vitamin $B_7$, vitamin $B_9$, vitamin $B_{12}$, zinc, selenium, L-cysteine, and glutathione.

In a preferred embodiment, the composition comprises about 450-600 mcg carotenoids, about 60 mg to 100 mg vitamin C, 375 IU to 425 IU vitamin D, 30 IU vitamin E, 25 mcg to 50 mcg vitamin K, 1 mg to 2 mg vitamin $B_1$, 1 mg to 2 mg vitamin $B_2$, 10 mg to 30 mg vitamin $B_3$, 5 mg to 10 mg vitamin $B_5$, 5 mg to 10 mg vitamin $B_6$, 150 mcg to 300 mcg vitamin $B_7$, 1 mg to 2 mg vitamin $B_9$, 10 mcg to 25 mcg vitamin $B_{12}$, 15 mcg to 30 mcg selenium, 5 mg to 10 mg zinc, 15 mg to 25 mg L-cysteine, and 15 mg to 25 mg glutathione (Table 5).

TABLE 5

Multivitamin and mineral compositions of the present invention

| Vitamin or Mineral | Composition of the Present Invention |
|---|---|
| Vitamin A | No Vitamin A is present. Carotenoids in doses ranging from 450 mcg to 600 mcg are provided. |
| Vitamin C | 60-100 mg |
| Vitamin D | 400-2000 IU |
| Vitamin E | 30-600 IU provided as combinations of the eight stereoisomeric forms of Vitamin E |
| Vitamin K | 25 mcg - 1 mg provided as combinations of Vitamin K1 and K2 |
| Thiamin/Vitamin $B_1$ | 1-2 mg |
| Riboflavin/Vitamin $B_2$ | 1-2 mg |
| Niacin/Vitamin $B_3$ | 10-30 mg |
| Pantothenic Acid/Vitamin $B_5$ | 5-10 mg |
| Vitamin $B_6$ | 5-10 mg |
| Biotin/Vitamin $B_7$ | 150-300 mcg |
| Folate/Vitamin $B_9$ | 0.8-5 mg |
| Vitamin $B_{12}$ Source | 10-25 mcg |
| Zinc | 5-10 mg |
| Selenium | 15-30 mcg |
| Anti-oxidant amino acids | 15-25 mg each of L-cysteine and glutathione or the mass equivalent to these weights of precursors to these amino acids |
| Other Components | Conventional formulation excipients that may be required as binders, fillers, glidants, and release agents, for example. FD&C Color additives that do not contain aluminum may be used. |

In a further preferred embodiment, the composition comprises about 500 mcg carotenoids, about 80 mg vitamin C, 400 IU vitamin D, 30 IU vitamin E, 25 mcg vitamin K, 1.2 mg vitamin $B_1$, 1.25 mg vitamin $B_2$, 15 mg vitamin $B_3$, 7.5 mg vitamin $B_5$, 6 mg vitamin $B_6$, 200 mcg vitamin $B_7$, 1.2 mg vitamin $B_9$, 18 mcg vitamin $B_{12}$, 20 mcg selenium, 7.5 mg zinc, 20 mg L-cysteine, and 20 mg glutathione.

TABLE 6

Preferred embodiment of a composition of the invention

| Vitamin or Mineral | Composition of the Present Invention |
|---|---|
| Carotenoids | 500 mcg |
| Vitamin C | 80 mg |
| Vitamin D | 600 IU |
| Vitamin E | 30 IU |
| Vitamin K | 25 mcg |
| Thiamin/Vitamin $B_1$ | 1.2 mg |
| Riboflavin/Vitamin $B_2$ | 1.25 mg |
| Niacin/Vitamin $B_3$ | 15 mg |
| Pantothenic Acid/Vitamin $B_5$ | 7.5 mg |
| Vitamin $B_6$ | 6 mg |
| Biotin/Vitamin $B_7$ | 200 mcg |
| Folate/Vitamin $B_9$ | 1.2 mg |
| Vitamin $B_{12}$ Source | 18 mcg |
| Zinc | 7.5 mg |
| Selenium | 20 mcg |
| Anti-oxidant amino acids | 20 mg each of L-cysteine and glutathione or the mass equivalent to these weights of precursors to these amino acids |
| Other Components | Conventional formulation excipients that may be required as binders, fillers, glidants, and release agents, for example. FD&C Color additives that do not contain aluminum may be used. |

In a further preferred embodiment of the present invention, the composition comprises combinations of 500 mcg carotenoids, 80 mg vitamin C, 600 IU vitamin D, 30 IU vitamin E, 50 mcg vitamin K, 1.2 mg vitamin $B_1$, 1.25 mg vitamin $B_2$, 15 mg vitamin $B_3$, 7.5 mg vitamin $B_5$, 6 mg vitamin $B_6$, 200 mcg vitamin $B_7$, 1.2 mg vitamin $B_9$, 18 mcg vitamin $B_{12}$, 20 mcg selenium, 7.5 mg zinc, 20 mg L-cysteine, and 20 mg of glutathione.

TABLE 7

Preferred embodiment of the present invention

| Vitamin or Mineral | Composition of the Present Invention |
|---|---|
| Carotenoids | 500 mcg |
| Vitamin C | 80 mg |
| Vitamin D | 600 IU |
| Vitamin E | 30 IU |
| Vitamin K | 50 mcg |
| Thiamin/Vitamin $B_1$ | 1.2 mg |
| Riboflavin/Vitamin $B_2$ | 1.25 mg |
| Niacin/Vitamin $B_3$ | 15 mg |
| Pantothenic Acid/Vitamin $B_5$ | 7.5 mg |
| Vitamin $B_6$ | 6 mg |
| Biotin/Vitamin $B_7$ | 200 mcg |
| Folate/Vitamin $B_9$ | 1.2 mg |
| Vitamin $B_{12}$ Source | 18 mcg |
| Zinc | 7.5 mg |
| Selenium | 20 mcg |
| Anti-oxidant amino acids | 20 mg each of L-cysteine and glutathione or the mass equivalent to these weights of precursors to these amino acids |
| Other Components | Conventional formulation excipients that may be required as binders, fillers, glidants, and release agents, for example. FD&C Color additives that do not contain aluminum may be used. |

In certain embodiments of compositions of the present invention, carotenoids are xanthophylls, carotenes, or both; vitamin C is ascorbic acid or the ascorbate compound known as Ester-C; vitamin E is combinations of stereoisomers of d-alpha tocopheryl acetate or d-alpha tocopheryl succinate; vitamin K is vitamins K1 and K2; niacin is niacin or niacinamide; pantothenic acid is d-calcium pantothenate, selenium is ebselen, L-selenomethionine, or sodium selenate; and zinc is zinc sulfate, zinc citrate, zinc lactate, or zinc tartrate; and L-cysteine is L-cysteine, N-acetyl-L-cysteine, or L-cystine.

While not wishing to be bound by any particular hypothesis or theory, the inventor bases his rationale for the compositions of his invention on his unique insights into data drawn from a spectrum of disparate clinical studies.

Role of carotenoids as Ssubstitutes for Vitamin A in Renal Patients

Humans and other animals are incapable of synthesizing carotenoids, and must obtain them through their diet. The most common carotenoids include lycopene, α-carotene, and the vitamin A precursor β-carotene. In plants, the xanthophyll lutein is the most abundant carotenoid, and its role in preventing age-related eye disease is currently under investigation. Crude palm oil is the richest source of carotenoids in nature.

Carotenoids have many physiological functions. Given their structure, carotenoids are efficient free-radical scavengers, and they enhance the vertebrate immune system. Investigators have found that the concentrations of carotenoids in patients with chronic renal failure are abnormally low. [Ha T K K, Sattar N, Talwar D, Cooney J, Simpson K, O'Reilly D S J, Lean M E J. Abnormal antioxidant vitamin and carotenoid status in chronic renal failure. Quarterly J Med 1996; 89(10): 765-769.] In a recent review, Winklhofer-Roob et al. have summarized the beneficial effects that correction of carotenoid status has on reducing the effects of oxidative stress in diseases such as CKD. [Winklhofer-Roob B M, Rock E, Ribalta J, Shmerling D H, Roob J M. Effects of vitamin E and carotenoid status on oxidative stress in health and disease.

Evidence obtained from human intervention studies. Mol Aspects Med. 2003 December; 24(6): 391-402.]

The inventor considered the following facts in determining an optimal daily dose of carotenoids. Firstly, administration of vitamin A is contraindicated in the incident dialysis population, but substitute substances are needed as precursors to vitamin A or to perform the physiological functions of vitamin A. Carotenes are precursors to vitamin A and perform physiological functions of vitamin A. Therefore, the inventor has determined that about 450 mcg to about 600 mcg of carotenoids are required to provide carotenoids exhibiting activity of vitamin A in compositions of the invention and about 500 mcg of carotenoids are provided in preferred embodiments of the invention.

Role of Supplementation with the B Vitamins in Patients with Kidney Failure

Thiamine (vitamin $B_1$) is a requisite precursor to thiamine pyrophosphate, a coenzyme for pyruvate dehydrogenase, α-ketoglutarate dehydrogenase, branched chain α-keto acid dehydrogenase and transketolase (Table 1). The activity of thiamine is inhibited by folate deficiency and malnutrition. Chronic renal failure patients placed on a low protein diet exhibited a thiamine deficiency. [Porrini M, Simonetti P, Ciappellano S, Testolin G, Gentile M G, Manna G, Fellin G, D'Amico G. Thiamin, riboflavin and pyridoxine status in chronic renal insufficiency. Int J Vitam Nutr Res. 1989; 59(3): 304-8.] In addition, erythrocyte transketolase activity was impaired in dialysis patients. [Descombes E, Hanck A B, Fellay G. Water soluble vitamins in chronic hemodialysis patients and need for supplementation. Kidney Int 1993; 43: 1319-28.] Hence, to correct for any potential thiamine deficiency in renal patients, compositions of the present invention also comprise thiamine, preferably in the amount ranging from about 1 to about 2 mg.

Riboflavin (vitamin $B_2$) is a central component of two flavin coenzymes, flavin mononucleotide (FMN) and flavin adenine dinucleotide (FAD) (Table 1). These flavoenzymes play a key role in the metabolism of fats, carbohydrates, and proteins. Renal patients prescribed a low protein diet demonstrated evidence of riboflavin deficiency. [Porrini et al, vide infra. Stein G, Sperschneider H, Koppe S. Vitamin levels in chronic renal failure and need for supplementation. Blood Purif 1985; 3(1-3): 52-62.] Thus, compositions of the present invention may comprise riboflavin, preferably in an amount ranging from about 1 to about 2 mg.

Nicotinamide adenine dinucleotide (NAD) and NAD phosphate (NADP) are active coenzymes of niacin (vitamin $B_3$) (Table 1). These coenzymes are involved in numerous enzymatic reactions such as glycolysis, fatty acid metabolism, and steroid synthesis. Niacin is also required for the synthesis of pyroxidine, riboflavin, and folic acid. Administration of niacin may also produce a reduction in total cholesterol, low-density lipoprotein (LDL), and very low-density lipoprotein (VLDL) levels and an increase in high-density lipoprotein (HDL) cholesterol. [Henkin Y, Oberman A, Hurst D C, Segrest J P. Niacin revisited: clinical observations on an important but underutilized drug. Am J Med 1991; 91(3): 239-46.] DeBari et al. have found a niacin deficiency was noted in dialysis patients, and reduced amounts of niacin have been demonstrated in a low protein renal diet. [DeBari V A, Frank O, Baker H, Needle M A. Water soluble vitamins in granulocytes, erythrocytes, and plasma obtained from chronic hemodialysis patients. Am J Clin Nutr 1984; 39(3): 410-5. Mackenzie JC. Nutrition and dialysis. World Rev Nutr Diet. 1971; 13: 194-276.] Thus, to maintain appropriate niacin levels in renal patients, compositions of the present invention comprise niacin, preferably in an amount ranging from about 10 to about 30 mg.

Pantothenic acid (vitamin $B_5$) is a component of coenzyme A which is required for the metabolism and synthesis of fatty acids, carbohydrates, proteins, cholesterol, steroid hormones, and neurotransmitters (Table 1). The coenzyme A complex also has a major role in the acetylation and acylation of numerous proteins. Low protein diets as are typically prescribed for renal patients provide a minimum amount of pantothenic acid. In addition, a decrease in pantothenic acid plasma levels was observed in dialysis patients. [Mackenzie, vide infra.] Therefore, to minimize a potential deficiency of pantothenic acid in renal patients, compositions of the present invention comprise pantothenic acid, preferably in an amount ranging from about 5 to about 10 mg.

Pyridoxine (vitamin $B_6$) is present in the body as seven forms: pyridoxine, pyridoxine 5'-phosphate, pyridoxal, pyridoxal 5'-phosphate (PLP), pyridoxamine, pyridoxamine 5'-phosphate, and 4-pyridoxic acid (PA) (Table 1). With the exception of PA, which is metabolically inactive, all forms of pyridoxine are interconverted. Vitamin B6 in its active forms is a cofactor in gluconeogenesis, amino acid metabolism, and erythrocyte metabolism. A high incidence of pyridoxine deficiency has been noted in both adult and pediatric chronic renal failure patients, as well as patients undergoing dialysis. [Stein et al., vide infra. Descombes et al., vide infra.] A deficiency in pyridoxine may be attributed to the suppressed immune function observed in chronic renal patients, as well as the increased plasma and tissue oxalate concentrations in renal failure. [Morgan S H, Maher E R, Purkiss P, Watts R W, Curtis J R. Oxalate metabolism in end-stage renal disease: the effect of ascorbic acid and pyridoxine. Nephrol Dial Transplant 1988; 3(1): 28-32. Morgan S H, Purkiss P, Watts R W, Mansell M A. Oxalate dynamics in chronic renal failure. Comparison with normal subjects and patients with primary hyperoxaluria. Nephron 1987; 46(3): 253-7.] In addition, it has been suggested that pyridoxine deficiency plays a role in homocysteinemia which has been observed in renal patients. [Dennis V W, Robinson K. Homocysteinemia and vascular disease in end-stage renal disease. Kidney Int Suppl 1996; 57: S11-7.] Hence, compositions of the present invention comprise pyridoxine, preferably in an amount ranging from about 5 to about 10 mg.

Biotin (Vitamin $B_7$) acts a coenzyme for a number of carboxylases and has an important role in gluconeogenesis, fatty acid metabolism, and amino acid metabolism (Table 1). It has been shown that biotin inhibits the effects of uremic toxins on tubulin polymerization. [Braguer D, Gallice P, Yatzidis H, Berland Y, Crevat A. Restoration by biotin of the in vitro microtubule formation inhibited by uremic toxins. Nephron 1991; 57(2): 192-6.] Furthermore, there is some evidence to suggest that chronic renal failure patients and dialysis patients are at a risk for the development of a biotin deficiency. [Mackenzie, vide infra.] In several dialysis patients diagnosed with uremic encephalopathy and neuropathy, symptoms of these disorders were alleviated by administration of biotin. [Livaniou E, Evangelatos G P, Ithakissios D S, Yatzidis H, Koutsicos D C. Serum biotin levels in patients undergoing chronic hemodialysis. Nephron 1987; 46(3): 331-2. Yatzidis H, Koutsicos D, Agroyannis B, Papastephanidis C, Francos-Plemenos M, Delatola Z. Biotin in the management of uremic neurologic disorders. Nephron 1984; 36(3): 183-6.] Thus, to maintain appropriate biotin levels in renal patients, compositions of the present invention comprise biotin preferably in an amount ranging from about 150 to about 300 mcg.

Folic acid (vitamin $B_9$) in its active form, tetrahydrofolate, is a coenzyme that is involved in the transfer of methyl groups and plays a role in DNA synthesis, purine synthesis, and amino acid synthesis (Table 1). Synthetic compositions such as MetaFolin (a tradename of Merck Eprova AG) are also suitable sources of folate. The metabolism of folic acid is altered by uremia, and the absorption of tetrahydrofolate is impaired in chronic renal failure patients. [Said H M, Vaziri N D, Kariger R K, Hollander D. Intestinal absorption of 5-methyltetrahydrofolate in experimental uremia. Acta Vitaminol Enzymol 1984; 6(4): 339-46.] Furthermore, the diet generally prescribed for renal patients tends to be low in folic acid content, and medications used by chronic renal failure patients may also inhibit the activity of folic acid. [Stein et al, vide infra.] Tissue uptake and utilization of folic acid are also altered in renal patients. The high incidence of homocysteinemia observed in chronic renal failure patients and the related risk of development of atherosclerosis suggest that folic acid supplementation may provide an effective method for managing this condition and also provide a cardio-protective effect. [Jamison R L, Hartigan P, Gaziano J M, Fortmann S P, Goldfarb D S, Haroldson J A, Kaufman J, Lavori P, McCully K S, Robinson K. Design and statistical issues in the homocysteinemia in kidney and end stage renal disease (HOST) study. Clin Trials 2004; 1(5): 451-60. Chiarello P G, Vannucchi M T, Moyses Neto M, Vannucchi H. Hyperhomocysteinemia and oxidative stress in hemodialysis: effects of supplementation with folic acid. Int J Vitam Nutr Res. 2003; 73(6): 431-8.] Therefore, in a preferred embodiment, compositions of the present invention comprise folic acid, preferably in an amount ranging from about 1 to about 2 mg.

Cyanocobalamin (vitamin $B_{12}$) is the pharmaceutical form of cobalamin which can be converted to the active coenzymes, methylcobalamin and 5'-deoxyadenosylcobalamin (Table 1). These coenzymes are necessary for folic acid metabolism, conversion of coenzyme A, and myelin synthesis. A deficiency of vitamin $B_{12}$ was observed in chronic renal failure patients and dialysis patients. In addition, slow nerve conduction velocities were also noted in dialysis patients. [Rostand S G. Vitamin B12 levels and nerve conduction velocities in patients undergoing maintenance hemodialysis. Am J Clin Nutr 1976; 29(7): 691-7.] Based on these observations, vitamin $B_{12}$ supplementation may be appropriate as a means to compensate for any deficiency. Furthermore, since vitamin B12 has a role in folic acid metabolism, supplementation may be effective in managing homocysteine levels in renal patients. Thus, the novel compositions of the present invention comprise cyanocobalamin, preferably in an amount ranging from about 10 to about 25 mcg.

Role of Supplementation with Higher Doses of Vitamin C in Patients with Kidney Failure The clearance of vitamin C (ascorbate) during hemodialysis at a blood flow of 200-300 mL/min is about 100 mL/min. As a result, 80-280 mg of ascorbate is lost in the dialysate during each hemodialysis session in patients not receiving vitamin C supplements, and plasma ascorbic acid levels decrease by about 40% to 50% following hemodialysis. Descombes et al. found that 27% of 43 maintenance hemodialysis patients had decreased plasma vitamin C levels after dialysis had been performed using low flux/low efficiency dialyzers, despite a supplement of 200 mg of vitamin C taken post-dialysis 2-3 times per week. [Descombes et al., vide infra.] It is reasonable to expect that serum levels of vitamin C will be even lower in patients dialyzed with high efficiency and/or high flux hemodialysis membranes that are used at the present time.

Oxalate, a metabolic end-product of ascorbic acid, reacts with calcium and magnesium ions to form insoluble salts that can precipitate in the kidneys, forming oxalate-containing kidney stones. Normally, ascorbic acid that exceeds physiological requirements and oxalate are eliminated in the urine. However, in patients with kidney failure there is an accumulation of both ascorbic acid and oxalate. As a result, excessive vitamin C intake may contribute to hyperoxalemia and oxalate deposition in soft tissues of chronic renal failure patients. Plasma oxalate levels are known to increase with oral supplementation of 0.5 to 1 g/day of ascorbic acid in maintenance hemodialysis patients. Recent studies have shown that 300 mg vitamin C given intravenously post-dialysis three times a week helps mobilize iron from tissue stores in iron overloaded hemodialysis patients, thereby improving responsiveness to erythropoietin. [Tarng D C, Wei Y H, Huang T P, Kuo B I, Yang W C. Intravenous ascorbic acid as an adjuvant therapy for recombinant erythropoietin in hemodialysis patients with hyperferritinemia. Kidney International 1999; 55:2477-86.] Over a period of two months, this therapy led to a modest increase in plasma oxalate from 49±17 to 60±13 μmol/L.

The inventor considered the following facts in determining an optimal daily dose of vitamin C. Firstly, in maintenance hemodialysis patients receiving dialysis with low efficiency/flux membranes, weekly administration of 400-600 mg vitamin C orally is not adequate in maintaining serum levels in 27% of patients, even though the bioavailability of vitamin C up to 200 mg/day is nearly 100%. [Descombes et al., vide infra.] Secondly, vitamin C, 900 mg/week intravenously, leads to modest though statistically insignificant increase in plasma oxalate levels. [Tarng et al., vide infra.] Other factors that further support increasing the previously recommended 60 mg/day vitamin C intake include high efficiency/flux membranes that are increasingly used, longer duration of dialysis sessions, and increasing age and consequently lower nutritional intake of the incident dialysis population. Therefore, the inventor has determined that about 60 to 100 mg of ascorbate is required to provide the levels of vitamin C needed by renal patients and about 80 mg of vitamin C is provided in a preferred composition of the invention.

Role of Vitamin D Supplementation in Patients with Kidney Failure

Vitamin D is essential for maintaining a healthy skeleton throughout life. The adult form of bone disease associated with vitamin D deficiency is osteomalacia. However, before overt clinical symptoms of vitamin D deficiency become apparent, a depletion of the vitamin may increase the risk of fracture. Many patients with osteoporotic fractures have low serum 25-hydroxy-vitamin D [25-(OH)-D] concentrations. Treatment with vitamin D and calcium increases bone mass and reduces the risk of fractures. In addition to its effect on the skeleton, vitamin D has important effects on other organ systems, and vitamin D deficiency may lead to muscle weakness, impaired macrophage function, and insulin resistance. Vitamin D also has an anti-proliferative action and a deficiency may predispose to malignancy.

Vitamin D status is most commonly assessed by measuring serum concentration of 25-hydroxy-vitamin D [25-(OH)-D], the major circulating metabolite of vitamin D. 25-(OH)-D is biologically inactive. However, synthesis of 1,25-$(OH)_2$-$D_3$ and 24,25-$(OH)_2$-$D_3$, the active metabolites of vitamin D, by target organs such as kidney, osteoblasts and macrophages in situ requires adequate availability of the substrate 25-(OH)-D. To determine prevalence of vitamin D deficiency in ESRD, serum 25-(OH)-D levels were measured in a diverse cohort of 142 maintenance hemodialysis patients at the end of summer, i.e., at the end of a season when vitamin D level are expected to peak. [Obatake N, Ishimura E, Tsuchida T, Hirowatari K, Naka H, Imanishi Y, Miki T, Inaba M, Nishizawa Y. Annual change in bone mineral density in predialysis patients with chronic renal failure: significance of a decrease in serum 1,25-dihydroxy-vitamin D. J Bone Miner Metab 2007; 25(1): 74-9.] In 73 of the 142 patients, serum 25-(OH)-D levels were again measured at the end of winter when levels are expected to reach their nadir. The results (Table 8) showed that at the end of summer, 90% of the individuals in the test cohort were Vitamin D sufficient or exhibited only a mild deficiency. In contrast, at the end of winter, individuals with moderate Vitamin D deficiency had increased by a factor of 4, and those with severe deficiency had increased from 6% to 28% of the test group. Prevalence of vitamin D deficiency significantly increased from 53% at the end of summer to 81% at the end of winter (P<0.001).

TABLE 8

Incidence of Vitamin D deficiency in ESRD patients

| Vitamin D Deficiency | Absent | Mild | Moderate | Severe | Mean ± S.D. |
|---|---|---|---|---|---|
| Serum 25-(OH)-D (ng/mL) | >20 | 13-20 | 10-12 | <10 | |
| End of Summer (n = 142) | 46% | 44% | 4% | 6% | 22 ± 12.8 |
| End of winter (n = 73) | 19% | 34% | 19% | 28% | 15 ± 6.1 |

In the past, doses of 1 mg or 40,000 IU of vitamin D2 or 100-500 mcg/day of calcidiol have been recommended to increase calcium absorption and doses of 50-100 mg/day have been recommended to improve osteotitis fibrosa. [Halloran B P, Schaefer P, Lifschitz M, Levens M, Goldsmith R S. Plasma vitamin D metabolite concentrations in chronic renal failure: effect of oral administration of 25-hydroxyvitamin D3. J Clin Endocrinol Metab. 1984; 59(6): 1063-9.] More recently, clinicians have proposed that 1000-2000 IU per day of vitamin D2 or D3 or of 20-30 mcg of 25-(OH)-D3 will maintain the plasma 25(OH)D3 concentration close to the upper limit of the reference population, with few if any side-effects. [Cunningham J, Makin H. How important is vitamin D deficiency in uraemia? Nephrol Dial Transplant. 1997; 12(1): 16-8. Fournier A, Fardellone P, Achard J M, Ghazali A, Pruna A, El Esper N, Moriniere P. Importance of vitamin D repletion in uraemia. Nephrol Dial Transplant. 1999; 14(4): 819-23.]

The inventor has discovered that these therapeutic approaches are obsolete today because of the risk of prolonged hypercalcemia resulting from the long half-life of 25-(OH)-D3 in renal patients. Further, he has discovered that a dose of 800 IU or 20 mcg of cholecalciferol does not cause an increase in calciuria in pre-dialysis patients nor hypercalcemia, although these complications are seen with doses in excess of 2400 IU or 60 mcg/day of cholecalciferol. Likewise, the inventor has discovered that repletion of vitamin D to achieve a plasma 25-(OH)-D concentration in the 80th percentile or higher of normal clinical values prevents renal osteodystrophy, Looser zones, and sub-periosteal resorption, despite the persistence of hypocalcemia, hyperphosphatemia and metabolic acidosis, or the use of calcium-aluminum free phosphate binders such as sevelamer salts. Therefore, a composition of the invention comprises 375 to 425 IU of vitamin D and a preferred embodiment of a composition of the invention provides 400 IU of vitamin D.

Role of Vitamin E Supplementation in Patients with Kidney Failure

Cardiac disease is the single most important cause of death among patients receiving long-term dialysis therapy, accounting for 44% of overall mortality. Compelling evidence now exists linking free radicals and consequent oxidative stress to the pathogenesis and progression of atherosclerosis. Free radicals induce non-enzymatic lipid peroxidation, which in turn leads to cellular damage. Serum malondialdehyde (MDA) is the breakdown product of the major radical chain reactions leading to oxidation of polyunsaturated fatty acids and thus serves as a marker of oxidative stress.

Mean serum and red cell MDA concentrations are significantly higher in dialysis patients with cardiovascular disease than in those without. A number of studies have confirmed the beneficial effects of vitamin E on reducing plasma and red cell MDA concentrations in renal patients. [Boaz M M Z, Biro A, Katzir Z, Green M, Fainaru M, Smetana S. Serum malondialdehyde and prevalent cardiovascular disease in hemodialysis. Kidney Int 1999; 56: 1078-1083. Giardini 0 T-GM, Lubrano R, Ricciardi-Tenore G, Bandino D, Silvi I, Paradisi C, Mannarino O, Citti G, Elli M, Casciani C. Effects of alpha-tocopherol administration on red blood cell membrane lipid peroxidation in hemodialysis patients. Clin Nephrol 1984; 21: 174-177. Taccone-Gallucci M L R, DelPrincipe D, Menichelli A, Giordani M, Citti G, Morosetti M, Meloni C, Mazzarella V, Meschini L, Tozzo C, Elli M, Giardini O, Casciani C. Platelet lipid peroxidation in haemodialysis patients: effects of vitamin E supplementation. Nephrol Dial Transplant 1989; 4: 975-978. Yalcin A Y M, Dilek K, Kilinc A, Taga Y, Emerk K. The effect of vitamin E therapy on plasma and erythrocyte lipid peroxidation in chronic hemodialysis patients. Clin Chim Acta 1989; 185: 109-112.]

The beneficial effect of exogenous vitamin E may be partly attributed to vitamin E deficiency in dialysis patients. Platelet vitamin E (μg/mg of proteins) was found to be significantly lower in hemodialysis patients versus control subjects (0.6±0.1 versus 0.9±0.2, P<0.005). [Taccone-Gallucci et al, vide infra.] The levels increased to the normal range after 15 days of treatment with 300 mg/day vitamin E. In another recent study, a significant increase in oxidant stress and a significant decrease in plasma vitamin E levels were present in non-diabetic chronic hemodialysis patients compared with normal control subjects. [Giray B, Kan E, Bali M, Hincal F, Basaran N. The effect of vitamin E supplementation on antioxidant enzyme activities and lipid peroxidation levels in hemodialysis patients. Clin Chim Acta. 2003; 338(1-2): 91-8.]

Dialysis patients receiving erythropoietin are often prescribed parenteral iron. Depolymerization of conventional parenteral iron-carbohydrate complexes releases free ionic iron. Furthermore, the change in pH that occurs when the polynuclear iron complexes come in contact with plasma may further induce depolymerization and formation of ferric hydroxide. Consistent with these in vitro results, a recent clinical study found that 8 of the 10 hemodialysis patients given 100 mg Fe(III) hydroxide sucrose complex intravenously had bleomycin-detectable free iron in the circulation. [Hodkova M, Dusilova-Sulkova S, Skalicka A, Kalousova M, Zima T, Bartunkova J. Influence of parenteral iron therapy and oral vitamin E supplementation on neutrophil respiratory burst in chronic hemodialysis patients. Ren Fail 2005; 27(2): 135-41.] That redox active iron is released by colloidal iron compounds in the circulation is further evidenced by the rise in plasma total peroxide and malondialdehyde concentrations within ten minutes following infusion of 100 mg iron sucrose complex. Hodkova et al found that a single oral dose of 1200

IU of vitamin E was effective in attenuating the oxidative stress induced by intravenous iron.

Exposure of blood to hemodialysis membranes stimulates free radical generation and thereby activates monocytes to produce pro-inflammatory cytokines such as IL-1β and IL-6. [Hodkova M, Dusilova-Sulkova S, Skalicka A, Kalousova M, Zima T, Bartunkova J. Influence of parenteral iron therapy and oral vitamin E supplementation on neutrophil respiratory burst in chronic hemodialysis patients. Renal Fail 2005; 27(2): 135-41.] Repeated exposure to the hemodialysis membranes induces a chronic inflammatory state associated with high serum levels of C-reactive protein and other markers of inflammation. Chronic inflammation is thought to induce and enhance atherosclerotic lesions. Vitamin E is known to inhibit free radical generation and cytokine production by monocytes and thereby is likely to reduce the chronic inflammation induced by uremia and hemodialysis. [Hodkova M, et al., vide infra.]

Therefore, compositions of the invention comprise about 30-300 IU of vitamin E, provided as combinations of the eight stereoisomeric forms of vitamin E, and a preferred embodiment of a composition of the invention provides 30 IU of vitamin D.

Role of Supplementation with Vitamin K in Patients with Kidney Failure

Vitamin K plays an important role in vascular calcification and maintenance of bone mass. Accumulating evidence suggests that vitamin K stimulates bone formation and inhibits bone resorption.

Vitamin K Deficiency Leads to Soft Tissue and Vascular Calcification

Vascular calcification is a major problem in uremic patients and is seen in association with occlusive disease of coronary, cerebral, peripheral, and mesenteric vasculature. The calcification seen on chest radiographs is a composite of both intimal and medial calcification. Intimal calcification occurs within the perimeter of the internal elastic lamina as part of the atherosclerotic plaque and is often seen as discrete, punctate lesions on radiographs. It is associated with inflammatory cells, lipid, and vascular smooth muscle cells. In contrast, medial calcification occurs as an independent process in the context of aging, diabetes, end stage renal disease, neuropathy, and a number of rare genetic syndromes. It is found in association with elastin and vascular smooth muscle cells and is often seen as linear deposits along the elastic lamellae that, when severe, resemble railroad tracks. The intimal, punctate pattern of calcification would be more highly correlated with coronary heart disease because it is part of the atherosclerotic plaque.

Calcification in the vasculature is a highly complex and regulated process resembling that in bone. Attention has focused on a number of proteins that appear to have regulatory roles in the calcification process and, in particular, on a group known as γ-carboxyglutamic acid (Gla) proteins. The Gla proteins contain an uncommon amino acid—Gla—formed by a vitamin K-dependent posttranslational modification of specific glutamic acid residues. The Gla residues appear to confer calcium-binding properties on these proteins. One of the Gla proteins, matrix-gla-protein (MGP), a 15 kDa protein with five gla residues that is found in many connective tissues is thought to act as an inhibitor of calcification because first it has been found in close association with areas of calcification with high levels of MGP message and protein levels being present in the macrophages and vascular smooth muscle cells present in human atherosclerotic plaques, and second, mice lacking this gene develop severe calcification in vasculature such as in the aorta and other extra-skeletal sites. [Luo G, Ducy P, McKee M D, al a. Spontaneous calcification of arteries and cartilage in mice lacking matrix GLA protein. Nature 1997; 386: 78-81]. Therefore, it is thought that vitamin K deficiency is causally associated with vascular and soft-tissue calcification.

Vitamin K Deficiency is Associated with Osteoporosis

Vitamin K dependent gamma-carboxylases are necessary for the posttranslational gamma-carboxylation of three bone-matrix proteins, a step necessary for their binding to hydroxyapatite. The production of dicarboxylic glutamyl residues enhances calcium binding. Osteocalcin is best studied of these. Osteocalcin is a 5 kDa protein primarily localized to bone, is synthesized by bone cells and in human bone is concentrated in osteocytes. Its release from the osteocytes may be a signal in the bone turnover cascade. Osteocalcin regulates mineral maturation and may inhibit mineral deposition in the bone. It may also regulate the activity of osteoclasts and their precursors. It may mark the turning point between bone formation and resorption. Serum osteocalcin measurements have proved valuable as a marker of bone turnover in metabolic bone diseases. Circulating serum osteocalcin is commonly undercarboxylated in patients with osteoporosis, especially those with hip fractures, and the defect responds to modest doses of vitamin K. The inventor has discovered that chronic dialysis patients are at a 3-4 fold higher risk of hip fracture, compared with age, gender and ethnically similar general population [Gupta A, Kallenbach L R, Divine G W: Increased risk of hip fractures in U.S. medicare end-stage renal disease patients. J. Am. Soc. Nephrol. 8: 552A, 1997]. Kohlmeier et al. have reported that suboptimal vitamin K in hemodialysis patients is associated with increased bone fracture risk, and during a four-year follow-up period, the 41 patients who never had a fracture had nearly three times higher phylloquinone concentrations than the 9 patients with fractures during this period (1.59 vs. 0.55 nmol/L, P<0.002) [Kohlmeier M, Saupe J, Shearer M J, Schaefer K, Asmus G. Bone health of adult hemodialysis patients is related to vitamin K status. Kidney Int. 1997 April; 51(4): 1218-21. Kohlmeier M, Saupe J, Drossel H J, Shearer M J. Variation of phylloquinone (vitamin K1) concentrations in hemodialysis patients. Thromb Haemost. 1995 November; 74(5): 1252-4.]

Vitamin K Deficiency in Uremic Patients

In dialysis patients a deficiency of vitamin K1 (phylloquinone) and K2 (menaquinone) has been reported. [Nagasawa Y, Fujii M, Kajimoto Y, Imai E, Hori M. Vitamin K2 and serum cholesterol in patients on continuous ambulatory peritoneal dialysis. Lancet. 1998; 351(9104): 724.] ESRD patients are at risk for vitamin K deficiency because this patient population is frequently treated with antibiotics prescribed for a variety of infections such as catheter related infections and nosocomial infections consequent to frequent hospitalizations. Since the contribution of gut bacteria to vitamin K balance may be reduced in ESRD patients they are predisposed to vitamin K deficiency and recommended daily intake (RDI) may be higher. The RDI for vitamin K in the general population is about 60 μg in adult females and about 70-80 μg in adult males. Excessive intake of vitamin K does not have any adverse effects other than interfering with and antagonizing the action of coumadin.

The inventor has discovered that the 10 mcg dose of vitamin K that is provided in conventional multivitamin preparations is too low. On the other hand, he has discovered that there are no untoward effects associated with a 1 mg dose of vitamin K given each day over several years in the general population. A composition of his invention comprises vitamin K in doses that are appropriate for subjects with renal disease and provides 25 to 1000 mcg of vitamin K, and a preferred embodiment of a composition of the invention provides 50 mcg of vitamin K.

Role of Zinc Supplementation in Patients with Kidney Failure

There are more than 200 zinc metalloenzymes, including aldolase, alcohol dehydrogenase, RNA polymerase, and protein kinase C. Zinc plays a role in numerous metabolic activities such as nucleic acid production, protein synthesis, and development of the immune system. [Zima T, Tesar V, Mestek O, Nemecek K. Trace elements in end-stage renal disease. 2. Clinical implication of trace elements. Blood Purif 1999; 17(4): 187-98.] Abnormalities of Zn metabolism are well documented in patients with chronic renal disease, especially those with nephrotic disease and uremia. [Mahajan S K. Zinc in kidney disease. J Amer Coll Nutr 1989; 8: 296-304.]

The normal serum/plasma concentration of zinc (Zn) is 0.69-1.21 mg/L. Hypozincemia is common in patients with end-stage renal disease (ESRD) treated with continuous ambulatory peritoneal dialysis (CAPD) or hemodialysis. Uremic patients have low levels of zinc in plasma, leucocytes and hair, compared with healthy controls. [Mahajan S K, Prasad A S, Rabbani P, Briggs W A, McDonald F D. Zinc metabolism in uremia. J Lab Clin Med 1979; 94: 693-8.] This and other studies have shown that leukocyte zinc content, which is a reliable indicator of total body zinc stores, was found to be significantly decreased in uremic patients when compared to normal controls.

The causes of Zn deficiency in kidney disease are not clear. Decreased dietary Zn intake and intestinal absorption, increased endogenous Zn secretion, and increased urinary Zn excretion (as in the nephrotic syndrome and in renal transplant recipients) all may contribute to altered Zn metabolism. Uremic patients have numerous obstacles to adequate feeding including appetite suppression, and/or lack of energy, motivation or resources to prepare or procure adequate meals. Zinc is also removed by hemodialysis. Dialytic loss of zinc further increases the dietary requirement to maintain balance in patients on maintenance hemodialysis. In patients with renal disease not receiving dialysis, recommended renal diets with 1-1.5 gm protein and 2 gm potassium per day only provide a maximum of 8-14 mg of zinc, often well short of the recommended daily allowance of 15 mg/day for healthy adults. Therefore, patients on hemodialysis are commonly deficient in zinc and need supplements regularly. [Thomson N M, Stevens B J, Humphery T J, Atkins R C. Comparison of trace elements in peritoneal dialysis, hemodialysis, and uremia. Kidney Int. 1983 January; 23(1):9-14. Muirhead N, Kertesz A, Flanagan P R, Hodsman A B, Hollomby D J, Valberg L S. Zinc metabolism in patients on maintenance hemodialysis. Am J. Nephrol. 1986; 6(6): 422-6.

Zn depletion may account for decreased taste, sexual and gonadal dysfunction, hyperprolactinemia, glucose intolerance, hyperlipidemia, growth retardation in children, neuropathy, anemia, abnormalities of neutrophil and lymphocyte function, and delayed wound healing. Hyopguesia and anorexia improve and caloric intake increases following zinc administration. [Atkin-Thor E, Goddard B W, O'Nion J, Stephen R L, Kolff W J. Hypoguesia and zinc depletion in chronic dialysis patients. Am J Clin Nutr 1978; 31: 1948.] Patients suffering from impotence subsequent to initiation of dialysis were relieved of symptoms subsequent to zinc administration. [Antoniou L S T, Shalhoub R, Smith J. Reversal of uraemic impotence by zinc. The Lancet 1977; October 29: 895-898.]. Furthermore, zinc supplementation led to an increase in plasma testosterone levels into the normal range in 50% of patients tested. Zinc has long been known to play a role in maintaining immunologic function. Kimmel et al. have studied the role of zinc in modulating immune response in ESRD by estimation of IL-1, calcitriol and tumor necrosis factor-alpha production by mononuclear cells from blood and peritoneal effluents of 22 patients with ESRD treated with CAPD [Kimmel P L, Phillips T M, Lew S Q, Langman C B. Zinc modulates mononuclear cellular calcitriol metabolism in peritoneal dialysis patients. Kidney Int 1996; 49: 1407-12.]. A zinc-concentration dependent increase in stimulated IL-1 alpha and -beta, and TNF-alpha release in both peripheral mononuclear cells and peritoneal macrophages from patients with ESRD treated with CAPD was observed. The effect was zinc specific, as it was not reproduced by copper or chloride supplementation. A zinc concentration dependent increase in peritoneal macrophage calcitriol release was also noted.

Addition of zinc to the dialysate in hemodialysis patients (400 µg/L) over a period of 6 months led to a significant increase in serum zinc level and increased intracellular content of ATP in lymphocytes. The latter effect is thought to be related to a direct effect of zinc on lymphocyte membranes, since zinc may increase the stability of cellular membranes and prevent lipid peroxidation. Zinc may also have direct effect on the thymus gland thereby increasing the levels of thymic hormone thymulin, which has the capacity to promote T-cell function. [Bonomini M, Di Paolo B, De Risio F, et al. Effects of zinc supplementation in chronic haemodialysis patients. Neph Dial Transplant 1993; 8: 1166-8. Travaglini P, Moriondo P, Togni E, et al. Effect of oral zinc administration on prolactin and thymulin circulating levels in patients with chronic renal failure. J Clin Endocrinol Metab 1989; 68: 186-90.] It has been proposed that zinc supplementation may restore impaired cell-mediated immunity and lymphocyte function. [Zima T, Tesar V, Mestek O, Nemecek K. Trace elements in end-stage renal disease. 2. Clinical implication of trace elements. Blood Purif. 1999; 17(4): 187-98]. ESRD patients are at risk for development of uremic and/or diabetic neuropathy. Zinc supplementation has been shown to improve nerve conduction velocity and symptoms of neuropathy.

The inventor has considered the following facts in determining zinc doses in compositions of the present invention. Zinc sulfate (220 mg tablet, 88 mg elemental zinc) is often prescribed in a dose of one tablet per day in dialysis patients. A number of conventional multivitamins contain 15 mg of elemental zinc, provided as zinc oxide. Zinc toxicity is seen at plasma levels around 700 mcg/dL, but Mahajan et al. have shown that daily oral 25 mg elemental zinc per over a period of 6 months by hemodialysis patients of significantly increases the plasma Zn levels from 81±8 mcg/dL to 110±14 µg/dL (p<0.005; plasma zinc in normal controls was 111±10 µg/dL), well below the level associated with zinc toxicity. [Mahajan et al, vide infra.] Therefore, compositions of the present invention provide zinc, preferably in an amount of about 5 to about 25 mg. and a preferred embodiment of a composition of the invention provides 10 mg of zinc.

Role of Selenium

Selenium is a component of the antioxidant enzyme, glutathione peroxidase, which plays a critical role in the control of oxygen metabolism, particularly catalyzing the breakdown of hydrogen peroxide. [Burk R F. Selenium, an antioxidant nutrient. Nutr Clin Care 2002; 5(2): 75-9.] Glutathione peroxidase prevents the generation of free radicals and decreases the risk of oxidative damage to numerous tissues, including the vascular system. [Holben D H, Smith A M. The diverse role of selenium within selenoproteins: a review. J Am Diet Assoc 1999; 99(7): 836-43.] Selenium deficiency leads to underactivity of selenium-dependent metalloenzymes, such as superoxide dismutase and glutathione peroxidase and consequently deficient elimination of toxic free radical species. Selenium deficiency has been linked to cancer, congestive cardiomyopathy, skeletal myopathy and immune dysfunction.

The RDI for selenium is 70 mcg in males and 55 mcg in females. The normal serum/plasma concentration of selenium is 81-185 mcg/L. The serum levels of selenium have been reported as normal in pre-dialysis renal failure patients and decreased in dialysis patients. Thus, the mean serum level of selenium in 10 patients on maintenance hemodialysis was 100 mcg/L versus 130 mcg/L in normal controls. Similar decrease in serum levels has been reported in patients undergoing peritoneal dialysis. [Wallaeys B, Cornelis R, Mees L, Lamiere N. Trace elements in serum, packed cells, and dialysate of CAPD patients. Kidney Int 1986; 30: 599-604.] There appears to be significant removal of selenium via the dialysate as suggested by undetectable concentrations in the fresh peritoneal dialysate (<2 µg/L) but >50% increase in the concentration of Se in the spent dialysate (3±2 µg/L). [Sandstead H. Trace elements in uremia and hemodialysis. Am J Clin Nutr 1980; 33: 1501-1508.]

End-stage renal disease is a state of inflammation induced by exposure to uremic toxins, dialyzer membranes or bacterial products in the dialysate. Consequently serum markers of inflammation such as C-reactive protein, IL-1, IL-6 are elevated in uremia. The role of selenium repletion in abrogating this inflammatory response has not been studied. However, systemic inflammatory response syndrome (SIRS) is a co-morbidity of renal disease. To determine the effect of selenium replacement on morbidity and mortality in patients with SIRS in the intensive care unit setting, a controlled, randomized prospective open-label pilot study was completed in which patients with and without selenium replacement were studied. The data showed that in Se treated patients, serum selenium levels and GSH-Px activity normalized within 3 days, whereas in untreated controls, both variables remained significantly low ($p<0.0001$). The APACHE III score decreased significantly in both groups but was significantly lower in the Se-treated group. Overall mortality in the Se− group was 52% vs. 33.5% in the Se+ group. In conclusion, selenium replacement in patients with SIRS seems to improve clinical outcome [Angstwurm M W, Schottdorf J, Schopohl J, Gaertner R. Selenium replacement in patients with severe systemic inflammatory response syndrome improves clinical outcome. Crit Care Med 1999; 27: 1807-13.] Therefore, the inventor expects that SIRS in patients with end-stage renal disease receiving dialysis may be ameliorated by selenium repletion.

Selenium deficiency in chronic dialysis patients is attributable to losses during dialysis therapy, and inadequate selenium intake. Several studies have demonstrated significant decreases in serum selenium, selenium-dependent enzymes, and increased lipid peroxidation in dialysis patients. [Zima T, Mestek O, Nemecek K, Bartova V, Fialova J, Tesar V, Suchanek M. Trace elements in hemodialysis and continuous ambulatory peritoneal dialysis patients. Blood Purif 1998; 16(5): 253-60.] Oral and intravenous selenium supplementation with either inorganic or organic selenium-containing moieties has proven to be effective in improving the selenium status and immune function of renal patients, while decreasing the levels of oxidative stress products. [Temple K A, Smith A M, Cockram D B. Selenate-supplemented nutritional formula increases plasma selenium in hemodialysis patients. J Ren Nutr 2000; 10(1): 16-23.] Therefore, compositions of the present invention comprise selenium in an amount from about 15 mcg to about 30 mcg.

Role of Cysteine and Glutathione in Kidney Failure

Cardiovascular disease is the major cause of morbidity and mortality in patients with end-stage renal failure. Increased free radical production and antioxidant depletion may contribute to the greatly increased risk of atherosclerosis in these patients. L-Cysteine and glutathione are physiological antioxidants which are known to detoxify free radicals and ameliorate oxidative damage. Conventional multivitamin and mineral supplements fail to provide anti-oxidants having these activities. Therefore, compositions of the present invention comprise the anti-oxidants L-cysteine and glutathione in an amount equivalent to from about 15 mg to about 25 mg of each anti-oxidant.

Dosage and Dosage Forms

The compositions of the present invention provide a combination of essential vitamins and minerals that work together with various metabolic systems and physiological responses of the human body. The ingredients of the present invention are preferably combined into a composition which may be in the form of a solid powder, caplets, tablets, lozenges, pills, capsules, or a liquid, and which may be administered alone or in suitable combination with other components.

A preferred dosage of the compositions of the present invention comprises an oral dosage form that consists of one or more unit doses for human oral consumption. If more than one unit dose is used, each individual unit dose may be identical to the other unit doses, or each may contain only some of the ingredients of the composition, so that the combination of the different unit doses comprises a composition of the present invention.

For example, the composition of the present invention may be administered in one or more tablets, caplets, or lozenges as practical for ease of administration. Each of the vitamins and minerals is commercially available, and can be blended to form a single composition or can form multiple compositions which may be co-administered.

To prepare the components of the present invention, each of the active ingredients may be combined in intimate admixture with a suitable carrier according to conventional compounding techniques. This carrier may take a wide variety of forms depending upon the form of the preparation desired for administration, e.g., oral, sublingual, nasal, topical patch, or parenteral. The composition may comprise one to three tablets, caplets or lozenges, the composition of each being identical to each other caplet or lozenge.

In preparing the composition in oral dosage form, any of the conventional media may be utilized. For liquid preparations (e.g., suspensions, elixirs, and solutions) media containing, for example, water, oils, alcohols, flavoring agents, preservatives, coloring agents and the like may be used. Carriers such as starches, sugars, diluents, granulating agents, lubricants, binders, disintegrating agents and the like may be used to prepare oral solids (e.g., powders, caplets, pills, tablets, capsules, and lozenges). Controlled release forms may also be used. Because of their ease in administration, caplets, tablets, pills, and capsules represent the most advantageous oral dosage until form, in which case solid carriers are employed. If desired, tablets may be sugar coated or enteric coated by standard techniques.

The present invention also relates to methods for exogenously supplementing nutrients in a patient having nutritional deficiencies. Specifically, the present invention relates to methods for supplementing nutrients in a patient comprising the step of administering to said patient a composition comprising carotenoids, vitamin C, vitamin D, vitamin E, vitamin K, vitamin $B_1$, vitamin $B_2$, vitamin $B_3$, vitamin $B_5$, vitamin $B_6$, vitamin $B_7$, vitamin $B_9$, vitamin $B_{12}$, selenium, zinc, L-cysteine, and glutathione.

Compositions of the present invention are preferably administered to patients in amounts that provide the supplementation required to alleviate the vitamin and mineral deficiencies associated with renal disease. In a preferred embodiment of the present invention, the composition comprises 450-600 mcg carotenoids, 60-100 mg of vitamin C, 400-1200 IU vitamin D, 30 IU vitamin E, 25-50 mcg vitamin K, 1-2 mg of vitamin $B_1$, 1-2 mg of vitamin $B_2$, 10-30 mg of vitamin $B_3$, 5-10 mg of vitamin $B_5$, 5-10 mg of vitamin $B_6$, 150-300 mcg of vitamin $B_7$, 1-2 mg of vitamin $B_9$, 10-25 mcg of vitamin $B_{12}$, 15-30 mcg of selenium, 5-10 mg of zinc, 15-25 mg of L-cysteine, and 15-25 mg of glutathione.

In a further preferred embodiment, the composition comprises about 500 mcg carotenoids, 80 mg vitamin C, 800 IU vitamin D, 30 IU vitamin E, 25 mcg vitamin K, 1.2 mg vitamin $B_1$, 1.25 mg vitamin $B_2$, 15 mg vitamin $B_3$, 7.5 mg vitamin $B_5$, 6 mg vitamin $B_6$, 200 mcg vitamin $B_7$, 1.2 mg vitamin $B_9$, 18 mcg vitamin $B_{12}$, 20 mcg selenium, 7.5 mg zinc, 20 mg L-cysteine, and 20 mg glutathione.

In a further preferred embodiment, the composition comprises about 500 mcg carotenoids, 80 mg vitamin C, 800 IU vitamin D, 30 IU vitamin E, 50 mcg vitamin K, 1.2 mg vitamin $B_1$, 1.25 mg vitamin $B_2$, 15 mg vitamin $B_3$, 7.5 mg vitamin $B_5$, 6 mg vitamin $B_6$, 200 mcg vitamin $B_7$, 1.2 mg vitamin $B_9$, 18 mcg vitamin $B_{12}$, 20 mcg selenium, 7.5 mg zinc, 20 mg L-cysteine, and 20 mg glutathione.

A method for supplementing nutrients in a patient or person in need thereof comprises the step of administering to said patient a composition comprising carotenoids, vitamin C, vitamin D, vitamin E, vitamin K, vitamin $B_1$, vitamin $B_2$, vitamin $B_3$, vitamin $B_5$, vitamin $B_6$, vitamin $B_7$, vitamin $B_9$, vitamin $B_{12}$, selenium, zinc, L-cysteine, and glutathione.

In a preferred embodiment of the present invention, the method for supplementing nutritional deficiencies in a patient or person in need thereof, comprises the step of administering to said patient a composition comprising composition comprises 450-600 mcg carotenoids, 60-100 mg of vitamin C, 400-1200 IU vitamin D, 30 IU vitamin E, 1-2 mg of vitamin $B_1$, 1-2 mg of vitamin $B_2$, 10-30 mg of vitamin $B_3$, 5-10 mg of vitamin $B_5$, 5-10 mg of vitamin $B_6$, 150-300 mcg of vitamin $B_7$, 1-2 mg of vitamin $B_9$, 10-25 mcg of vitamin $B_{12}$, 15-30 mcg of selenium, 5-10 mg of zinc, 15-25 mg of L-cysteine, and 15-25 mg of glutathione.

In a further preferred embodiment, the methods of the present invention comprise administering to a patient a composition comprising about 500 mcg carotenoids, 80 mg vitamin C, 800 IU vitamin D, 30 IU vitamin E, 25 mcg vitamin K, 1.2 mg vitamin $B_1$, 1.25 mg vitamin $B_2$, 15 mg vitamin $B_3$, 7.5 mg vitamin $B_5$, 6 mg vitamin $B_6$, 200 mcg vitamin $B_7$, 1.2 mg vitamin $B_9$, 18 mcg vitamin $B_{12}$, 20 mcg selenium, 7.5 mg zinc, 20 mg L-cysteine, and 20 mg glutathione.

In a further preferred embodiment, the methods of the present invention comprise administering to a patient a composition comprising about 500 mcg carotenoids, 80 mg vitamin C, 800 IU vitamin D, 30 IU vitamin E, 50 mcg vitamin K, 1.2 mg vitamin $B_1$, 1.25 mg vitamin $B_2$, 15 mg vitamin $B_3$, 7.5 mg vitamin $B_5$, 6 mg vitamin $B_6$, 200 mcg vitamin $B_7$, 1.2 mg vitamin $B_9$, 18 mcg vitamin $B_{12}$, 20 mcg selenium, 7.5 mg zinc, 20 mg L-cysteine, and 20 mg glutathione.

These methods also preferably comprise the administration of one or more of the compositions of the present invention to a patient afflicted with renal disease or renal insufficiency. In a preferred embodiment of the present invention, the methods preferably comprise the administration of one or more of the compositions to a patient suffering from end-stage renal disease and undergoing dialysis treatment. In a further preferred embodiment, the methods preferably comprise the administration of one or more of the compositions of the present invention to treat the nutritional deficiencies of any disease state that results in increased oxidative stress, elevated cholesterol levels, or elevated homocysteine levels.

Other objectives, features and advantages of the present invention will become apparent from the following specific examples. The specific examples, while indicating specific embodiments of the invention, are provided by way of illustration only. Accordingly, the present invention also includes those various changes and modifications within the spirit and scope of the invention that may become apparent to those skilled in the art from this detailed description. The invention will be further illustrated by the following non-limiting examples.

Example 1

A composition of the following formulation was prepared in caplet form using conventional methods known to those skilled in the pharmaceutical and formulary arts.

| Vitamin or Mineral | Composition of the Present Invention |
|---|---|
| Lycopene (a carotenoid) | 500 mcg |
| Vitamin C | 80 mg |
| Vitamin D | 800 IU |
| Vitamin E | 30 IU, provided as a combination of the eight stereoisomeric forms of Vitamin E |
| Vitamin K | 25 mcg, provided as a combination of Vitamin $K_1$ and $K_2$ |
| Thiamin/Vitamin $B_1$ | 1.2 mg |
| Riboflavin/Vitamin $B_2$ | 1.25 mg |
| Niacin/Vitamin $B_3$ | 15 mg |
| Pantothenic Acid/Vitamin $B_5$ | 7.5 mg |
| Vitamin $B_6$ | 6 mg |
| Biotin/Vitamin $B_7$ | 200 mcg |
| Folate/Vitamin $B_9$ | 1.2 mg |
| Vitamin $B_{12}$ Source | 18 mcg |
| Zinc | 7.5 mg |
| Selenium | 20 mcg |
| Anti-oxidant amino acids | 20 mg each of N-acetyl L-cysteine and glutathione |

One (1) caplet equals a unit dose. One caplet per day is the recommended dosage or a unit dose is administered as prescribed by a physician.

Example 2

A study is undertaken to evaluate the effectiveness of the composition of the present invention of Example 1 in the treatment of patients diagnosed with end-stage renal disease (ESRD). The objective of the study is to determine whether oral intake of the composition results in an improvement of the nutritional status of the patient.

A double-blind, placebo-controlled study is conducted over a 12-month period. A total of 100 subjects (50 men and 50 women) aged 25 to 85 years, suffering from ESRD and undergoing dialysis treatment, are enrolled in the study. The 100 subjects are separated into two groups, each group comprising 25 men and 25 women. Each subject in Group A, the Test Group, is administered 1 caplet, daily, of the composition as described in Example 1. Each subject in Group B, the Control Group, is administered a placebo caplet, daily.

Prior to the initiation of dosing, an initial assessment of nutritional status of each subject in both groups is conducted. The assessment includes clinical determinations of nutritional status and an interview with each subject to determine their personal beliefs regarding their health, well-being and quality of life using a standardized questionnaire. Data from the clinical assessment constitute the baseline values for the subject. For clinical assessment, a blood sample is obtained from each subject. A serum sample and a packed red blood cells sample are prepared from the blood sample. Ascorbate, selenium and zinc levels in each serum sample are measured using spectrophotometric and calorimetric methods. Vitamin $B_9$ and vitamin $B_{12}$ levels in each serum sample are measured by radioimmunoassay. Vitamin $B_6$ and vitamin $B_7$ levels in each serum sample are determined by high performance liquid chromatography (HPLC). Vitamin $B_3$ levels in each urine sample are determined by measuring known metabolic products. Vitamin E in the red blood cells sample is measured by the peroxide hemolysis test, and vitamin $B_1$ is measured by determining erythrocyte transketolase activity. Vitamin $B_2$ levels are determined by measuring erythrocyte glutathione reductase activity, and vitamin $B_5$ levels are determined by measuring erythrocyte coenzyme A activity.

At one-month intervals for the twelve-month period of the study, an assessment of the nutritional status of each subject in both groups is completed as described above. The data are compiled and evaluated using multiple linear regression analysis, analysis of variance, and a standard student's t-test to compare each subject's data at each interval with the baseline values for that subject. In addition, the data are grouped to enable a comparison of the average baseline values for the group with the average values obtained at each test interval.

A statistically significant improvement in the nutritional status is observed in the treated subjects (Group A) but not the controls (Group B). The differences between nutritional state of the treated subjects and controls are statistically significant. In addition, when interviewed, treated subjects report a general improvement in health and well-being. Therefore, the study confirms that oral administration of the composition of the present invention is effective in the treatment of patients diagnosed with ESRD.

The disclosures of all references and publications cited above are expressly incorporated by reference in their entireties to the same extent as if each were incorporated by reference individually. Various modifications and variations of the methods and compositions of the invention disclosed herein will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention, which are obvious to those skilled in the art, are intended to be within the scope of the following claims.

I claim:

1. A nutrient composition for treating nutritional deficiencies in an individual or patient in need thereof, comprising an oral dosage form including carotenoids, vitamin C, vitamin D, vitamin E, vitamin K, vitamin $B_1$, vitamin $B_2$, vitamin $B_3$, vitamin $B_5$, vitamin $B_6$, vitamin $B_7$, vitamin $B_9$, vitamin $B_{12}$, selenium, zinc, L-cysteine, and glutathione, said composition being free of vitamin A and salts and/or esters of vitamin A.

2. The nutrient composition of claim 1, wherein said composition is substantially free of other vitamins and minerals.

3. The composition of claim 1, comprising 450-600 mcg carotenoids, 60-100 mg vitamin C, 400-1200 IU vitamin D, 30 IU vitamin E, 25-50 mcg vitamin K, 1-2 mg vitamin $B_1$, 1-2 mg vitamin $B_2$, 10-30 mg vitamin $B_3$, 5-10 mg vitamin $B_5$, 5-10 mg vitamin $B_6$, 150-300 mcg vitamin $B_7$, 1-2 mg vitamin $B_9$, 10-25 mcg vitamin $B_{12}$, 15-30 mcg selenium, 5-10 mg zinc, 15-25 mg L-cysteine, and 15-25 mg glutathione.

4. The composition of claim 1, comprising 500 mcg carotenoids, 80 mg vitamin C, 800 IU vitamin D, 30 IU vitamin E, 25 mcg to 50 mcg vitamin K, 1.2 mg vitamin $B_1$, 1.25 mg vitamin $B_2$, 15 mg vitamin $B_3$, 7.5 mg vitamin $B_5$, 15 mg vitamin $B_6$, 200 mcg vitamin $B_7$, 1.2 mg vitamin $B_9$, 18 mcg of vitamin $B_{12}$, 20 mcg of selenium, 7.5 mg zinc, 20 mg of L-cysteine, and 20 mg of glutathione.

5. The composition of claim 1, wherein said composition is in a powder, caplet, tablet, lozenge, pill, capsule, or liquid dosage form.

6. The composition of claim 1, wherein said composition further comprises a pharmaceutically acceptable carrier.

7. A method for supplementing nutrients in a subject having nutritional deficiencies comprising the step of administering to said subject a composition in oral dosage form comprising 450-600 mcg carotenoids, 60-100 mg vitamin C, 400-800 IU vitamin D, 30 IU vitamin E, 25-50 mcg vitamin K, 1-2 mg vitamin $B_1$, 1-2 mg vitamin $B_2$, 10-30 mg vitamin $B_3$, 5-10 mg vitamin $B_5$, 5-10 mg vitamin $B_6$, 150-300 mcg vitamin $B_7$, 1-2 mg vitamin $B_9$, 10-25 mcg vitamin $B_{12}$, 15-30 mcg selenium, 5-10 mg zinc, 15-25 mg L-cysteine, and 15-25 mg glutathione, said composition being free of vitamin A and salts and/or esters of vitamin A.

8. The method of claim 7, wherein said composition comprises 500 mcg carotenoids, 80 mg vitamin C, 800 IU vitamin D, 30 IU vitamin E, 25 mcg or 50 mcg vitamin K, 1.2 mg vitamin $B_1$, 1.25 mg vitamin $B_2$, 15 mg vitamin $B_3$, 7.5 mg vitamin $B_5$, 15 mg vitamin $B_6$, 200 mcg vitamin $B_7$, 1.2 mg vitamin $B_9$, 18 mcg of vitamin $B_{12}$, 20 mcg of selenium, 7.5 mg zinc, 20 mg of L-cysteine, and 20 mg of glutathione.

9. The method of claim 7, wherein said composition is substantially free of other vitamins and minerals.

10. The method of claim 7, wherein said composition is administered to said individual or patient daily.

11. The method of claim 7, wherein said composition further comprises a pharmaceutically acceptable carrier.

12. The method of claim 7, wherein said composition is administered to an individual suffering from kidney disease.

13. The method of claim 7, wherein said composition is administered to an individual having Stage IV or V kidney disease.

14. The method of claim 7, wherein said composition is administered to an individual undergoing dialysis therapy.

* * * * *